United States Patent
Mulfinger

(10) Patent No.: US 12,318,546 B2
(45) Date of Patent: *Jun. 3, 2025

(54) RESPIRATOR WITH A MIXING CHAMBER, AND MIXING CHAMBER FOR A RESPIRATOR

(71) Applicant: Loewenstein Medical Technology S.A., Luxembourg (LU)

(72) Inventor: Jonas Mulfinger, Neu-Anspach (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 79 days.

This patent is subject to a terminal disclaimer.

(21) Appl. No.: 18/313,496

(22) Filed: May 8, 2023

(65) Prior Publication Data
US 2023/0270969 A1   Aug. 31, 2023

Related U.S. Application Data

(63) Continuation of application No. 16/808,482, filed on Mar. 4, 2020, now Pat. No. 11,679,225.

(30) Foreign Application Priority Data

Mar. 7, 2019   (DE) .......................... 102019001657.2

(51) Int. Cl.
*A61M 16/12* (2006.01)
*A61M 16/00* (2006.01)
(Continued)

(52) U.S. Cl.
CPC ............ *A61M 16/12* (2013.01); *A61M 16/01* (2013.01); *A61M 16/024* (2017.08);
(Continued)

(58) Field of Classification Search
CPC .............. A61M 16/00; A61M 16/0057; A61M 16/0063; A61M 16/0066; A61M 16/022;
(Continued)

(56) References Cited

U.S. PATENT DOCUMENTS 3,414,232 A   12/1968   Hellman
4,576,195 A   3/1986   Hahn et al.
(Continued)

FOREIGN PATENT DOCUMENTS

| AU | 2015275344 A1 | 7/2016 |
|---|---|---|
| CN | 102139133 A | 8/2011 |

(Continued)

OTHER PUBLICATIONS

Conrad, K.-J. (2013) Grundlagen der Konstruktionslehre (6th edition), Carl Hanser Verlag GmbH % Co. KG, pp. 282-283.
(Continued)

*Primary Examiner* — Joseph D. Boecker
(74) *Attorney, Agent, or Firm* — Abel Schillinger, LLP

(57) ABSTRACT

Disclosed is a respirator which comprises an electronic control device and a pneumatic main line in which the following are connected pneumatically: a respiratory gas source, a valve, a mixing chamber, a gas-dosing unit, and a supply line. The gas-dosing unit is configured to convey external air and/or oxygen and/or anesthetic gas into the mixing chamber, the respiratory gas source is configured to deliver respiratory gas to the supply line, the mixing chamber is configured to make available respiratory gas, the supply line is configured to supply the patient with respiratory gas, and the valve is configured to at least temporarily reduce a stream of respiratory gas to a patient.

20 Claims, 10 Drawing Sheets

(51) Int. Cl.
*A61M 16/01* (2006.01)
*A61M 16/08* (2006.01)
*A61M 16/10* (2006.01)
*A61M 16/20* (2006.01)

(52) U.S. Cl.
CPC ........ *A61M 16/104* (2013.01); *A61M 16/125* (2014.02); *A61M 16/203* (2014.02); *A61M 16/204* (2014.02); *A61M 16/0066* (2013.01); *A61M 16/08* (2013.01); *A61M 16/1005* (2014.02); *A61M 2202/0208* (2013.01); *A61M 2202/0241* (2013.01)

(58) Field of Classification Search
CPC ................ A61M 16/024; A61M 16/10; A61M 16/1005; A61M 16/104; A61M 16/12; A61M 16/122; A61M 16/125; A61M 16/20; A61M 16/203; A61M 16/204; A61M 2202/0208; A61M 2202/0241
See application file for complete search history.

(56) References Cited

U.S. PATENT DOCUMENTS

| | | | |
|---|---|---|---|
| 5,038,770 A | 8/1991 | Perkins | |
| 5,048,515 A | 9/1991 | Sanso | |
| 5,273,031 A | 12/1993 | Olsson et al. | |
| 5,596,984 A | 1/1997 | O'Mahony | |
| 5,605,148 A | 2/1997 | Jones | |
| 5,701,883 A | 12/1997 | Hete et al. | |
| 6,082,705 A * | 7/2000 | Arvidsson | A61M 16/206 251/129.17 |
| 6,095,496 A | 8/2000 | Rydin et al. | |
| 6,269,811 B1 | 8/2001 | Duff et al. | |
| 10,226,591 B1 * | 3/2019 | Tarler | A61M 16/022 |
| 11,679,225 B2 * | 6/2023 | Mulfinger | A61M 16/01 128/203.14 |
| 2002/0005197 A1 | 1/2002 | Devries | |
| 2002/0053345 A1 | 5/2002 | Jafari et al. | |
| 2003/0084900 A1 | 5/2003 | Leclerc | |
| 2006/0278231 A1 | 12/2006 | Nguyen | |
| 2007/0044799 A1 | 3/2007 | Hete et al. | |
| 2008/0092891 A1 | 4/2008 | Cewers | |
| 2008/0121233 A1 * | 5/2008 | von Blumenthal | A61M 16/12 128/204.22 |
| 2009/0007912 A1 | 1/2009 | Lindell et al. | |
| 2010/0078016 A1 | 4/2010 | Andrieux et al. | |
| 2010/0236635 A1 | 9/2010 | Tatarek | |
| 2011/0197884 A1 | 8/2011 | Duff et al. | |
| 2012/0006326 A1 * | 1/2012 | Ahmad | A61M 16/021 128/204.22 |
| 2012/0325208 A1 | 12/2012 | Heesch | |
| 2013/0008444 A1 * | 1/2013 | Chalvignac | A61M 16/201 128/204.21 |
| 2013/0087146 A1 | 4/2013 | Callaghan | |
| 2013/0087149 A1 | 4/2013 | Davidson et al. | |
| 2013/0239968 A1 | 9/2013 | Friberg et al. | |
| 2015/0273167 A1 | 10/2015 | Feldhahn et al. | |
| 2015/0320951 A1 | 11/2015 | Acker et al. | |
| 2015/0320953 A1 | 11/2015 | Acker | |
| 2015/0328417 A1 * | 11/2015 | Löser | A61M 16/024 128/204.23 |
| 2016/0131264 A1 | 5/2016 | Bregazzi et al. | |
| 2016/0256656 A1 | 9/2016 | Glenn et al. | |
| 2016/0287824 A1 * | 10/2016 | Chang | A61M 16/0066 |
| 2018/0051623 A1 | 2/2018 | Zhang | |
| 2018/0177961 A1 * | 6/2018 | Kagan | A61M 16/0883 |
| 2018/0224005 A1 | 8/2018 | Mayer | |
| 2018/0249763 A1 | 9/2018 | Schmidt et al. | |
| 2018/0280654 A1 | 10/2018 | Borrello | |
| 2019/0054265 A1 | 2/2019 | Shahar et al. | |
| 2019/0255276 A1 | 8/2019 | Van Schalkwyk et al. | |

FOREIGN PATENT DOCUMENTS

| | | |
|---|---|---|
| CN | 105727412 A | 7/2016 |
| DE | 2424025 B1 | 11/1975 |
| DE | 29622617 U1 | 3/1997 |
| DE | 19640113 C1 | 10/1997 |
| DE | 19907362 A1 | 8/2000 |
| DE | 102006055779 B3 | 3/2008 |
| DE | 102007053503 A1 | 5/2009 |
| DE | 102011012125 A1 | 8/2012 |
| DE | 102014001218 A1 | 7/2015 |
| DE | 102014109394 A1 | 1/2016 |
| DE | 102015208189 A1 | 2/2016 |
| EP | 0729762 A1 | 9/1996 |
| EP | 2425869 A1 | 3/2012 |
| GB | 2130402 A | 5/1984 |
| WO | 0228460 A1 | 4/2002 |
| WO | 2016140980 A1 | 9/2016 |
| WO | 2017055995 A1 | 4/2017 |

OTHER PUBLICATIONS

Feldhusen, J. et al., (2013), Pahl/Beitz Konstruktionslehre (8th edition), Springer-Verlag Bretlin Heidelberg, pp. 715-717.
ISO 80601-2-12: Apr. 15, 2011 Medical electrical equipment—Part 2-12: Particular requirments for basic safety and essential performance of critical care ventilators.
Draeger Medical GmbH (2015) Gebrauchsanweisung Infinity Acute Care System—Workstation Critical Care and Workstation Neonatal Care (3rd edition).
https://en.wikipedia.org/wiki/solenoid_valve, version archived by Wayback-Machine on Mar. 6, 2018 (https://web.archive.org/web/20180603004619/https://en.wikipedia.org/wiki/solenoid_valve) accessed Jul. 17, 2023.
https://tameson.com/solenoid-valve-types.html, version archived by Wayback-Machine (https://web.archive.org/web/20170930181600/) accessed Jul. 17, 2023.
Festo GmbH & Co. KG (2013) : White Paper: Piston spool valves and poppet valves—a technical comparison of available solenoid valves.
GSR Ventiltechnik GmbH & Co. KG (2006) Bedienungsanleitung fuer direkt gesteuerte Magnetventile.

* cited by examiner

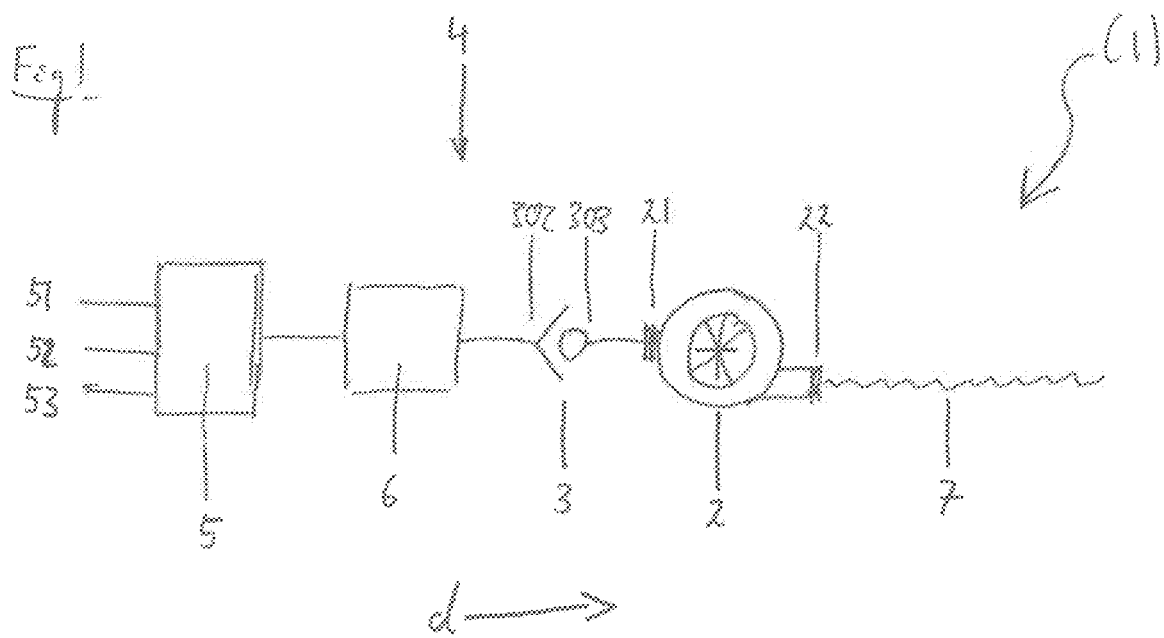
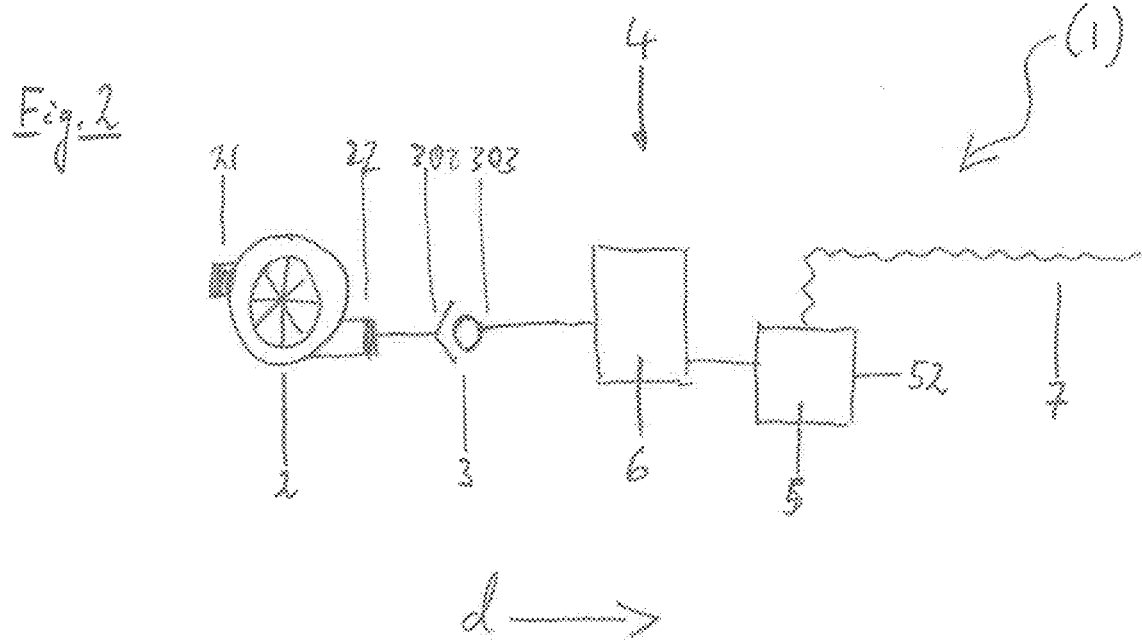

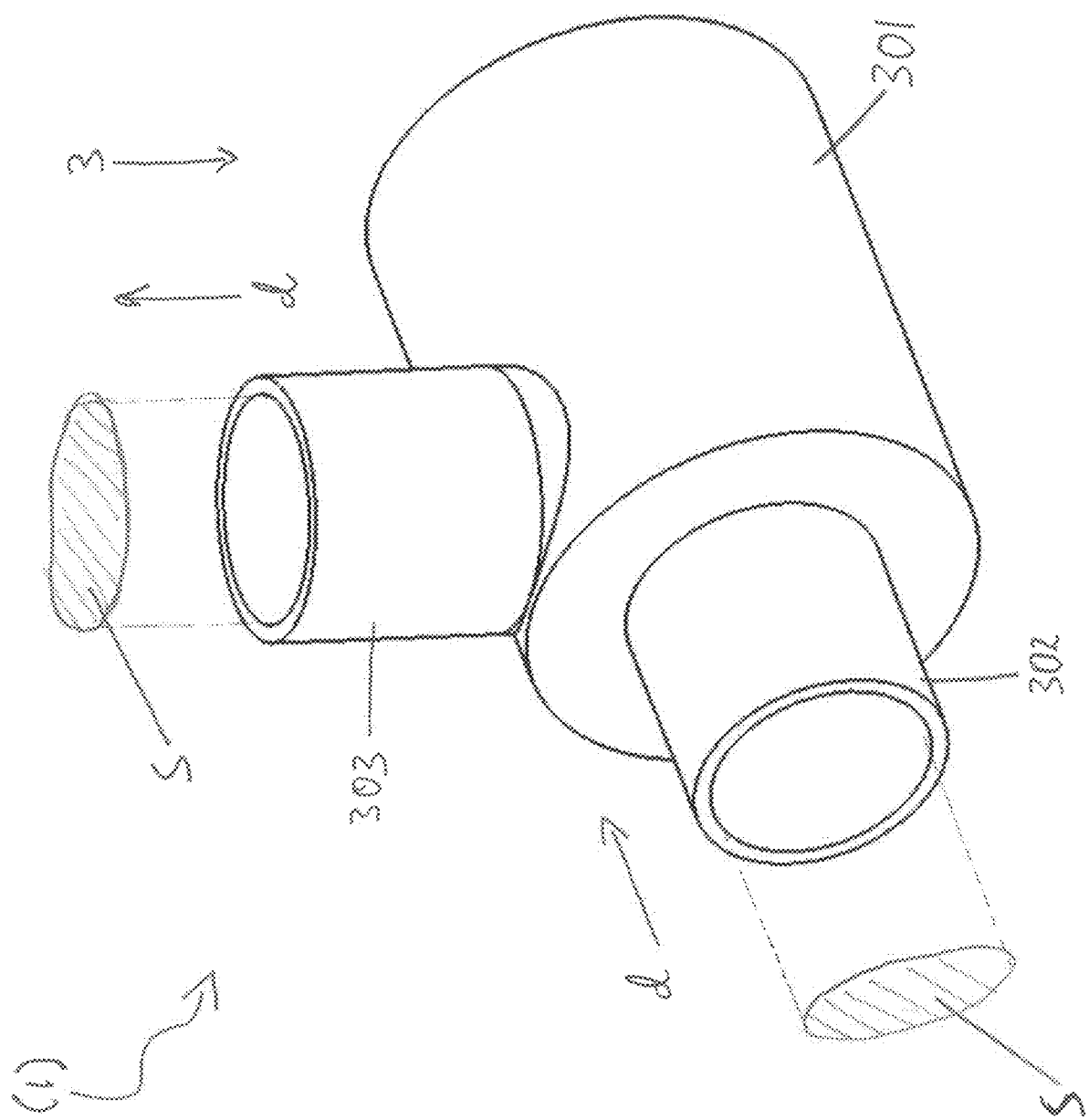

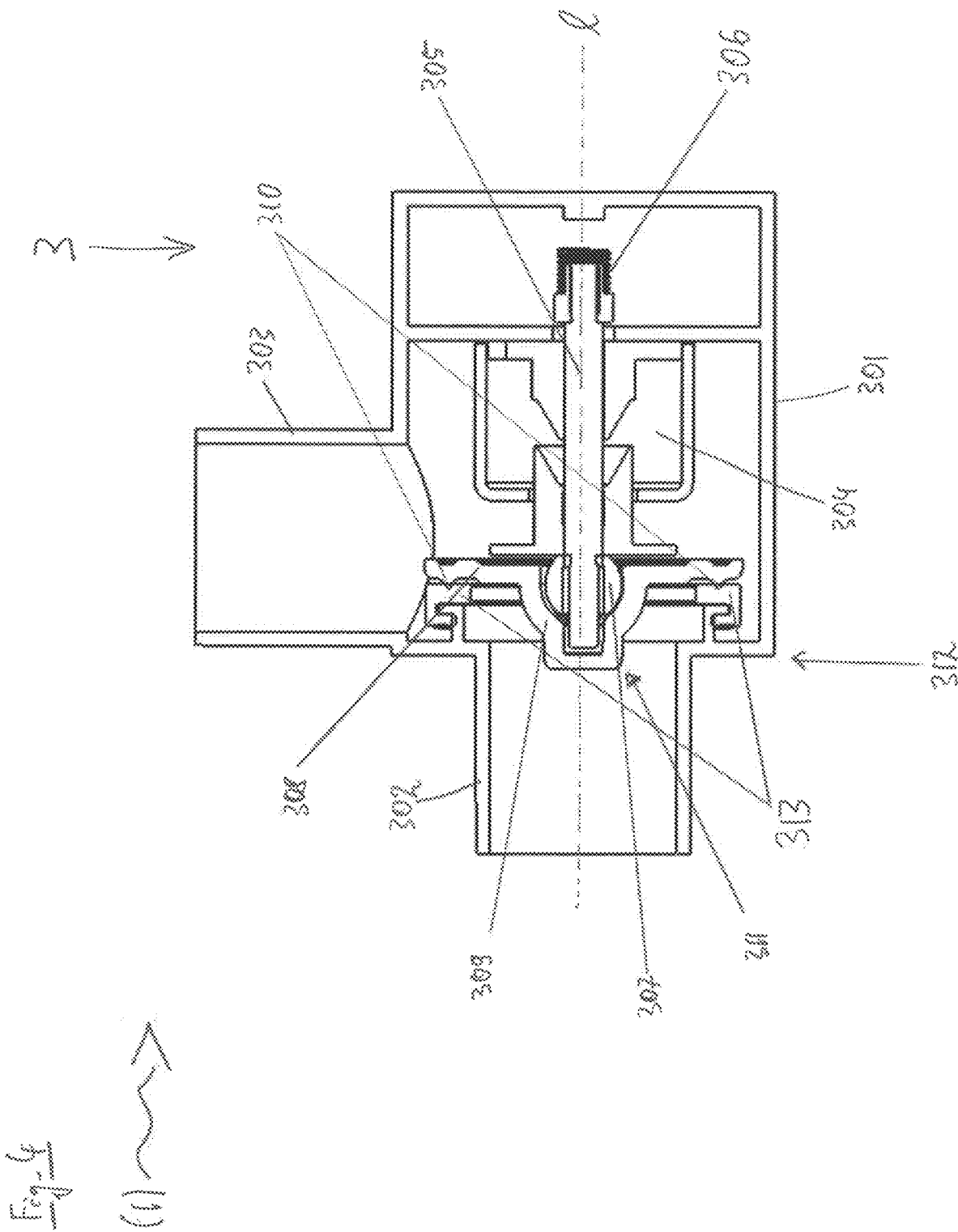

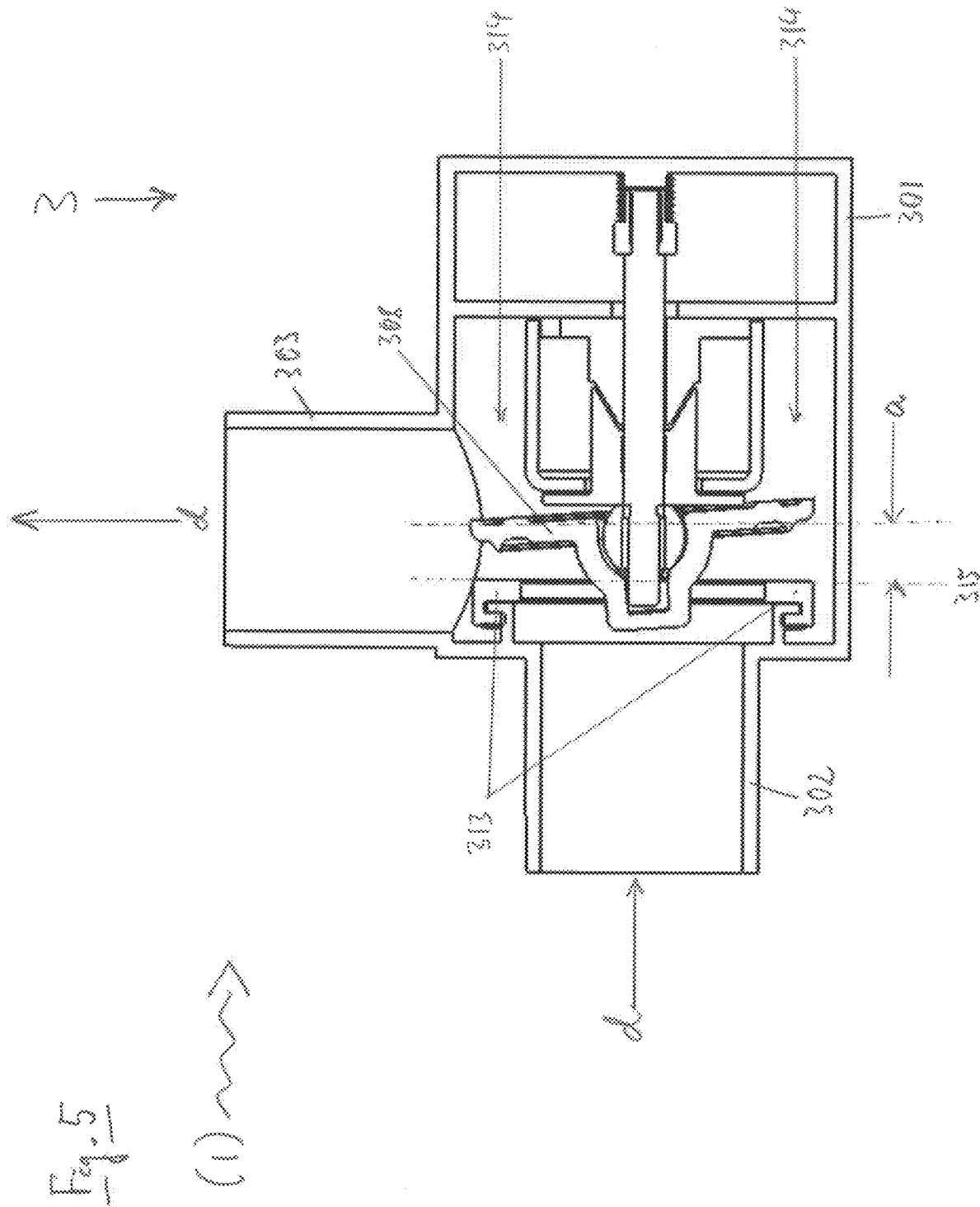

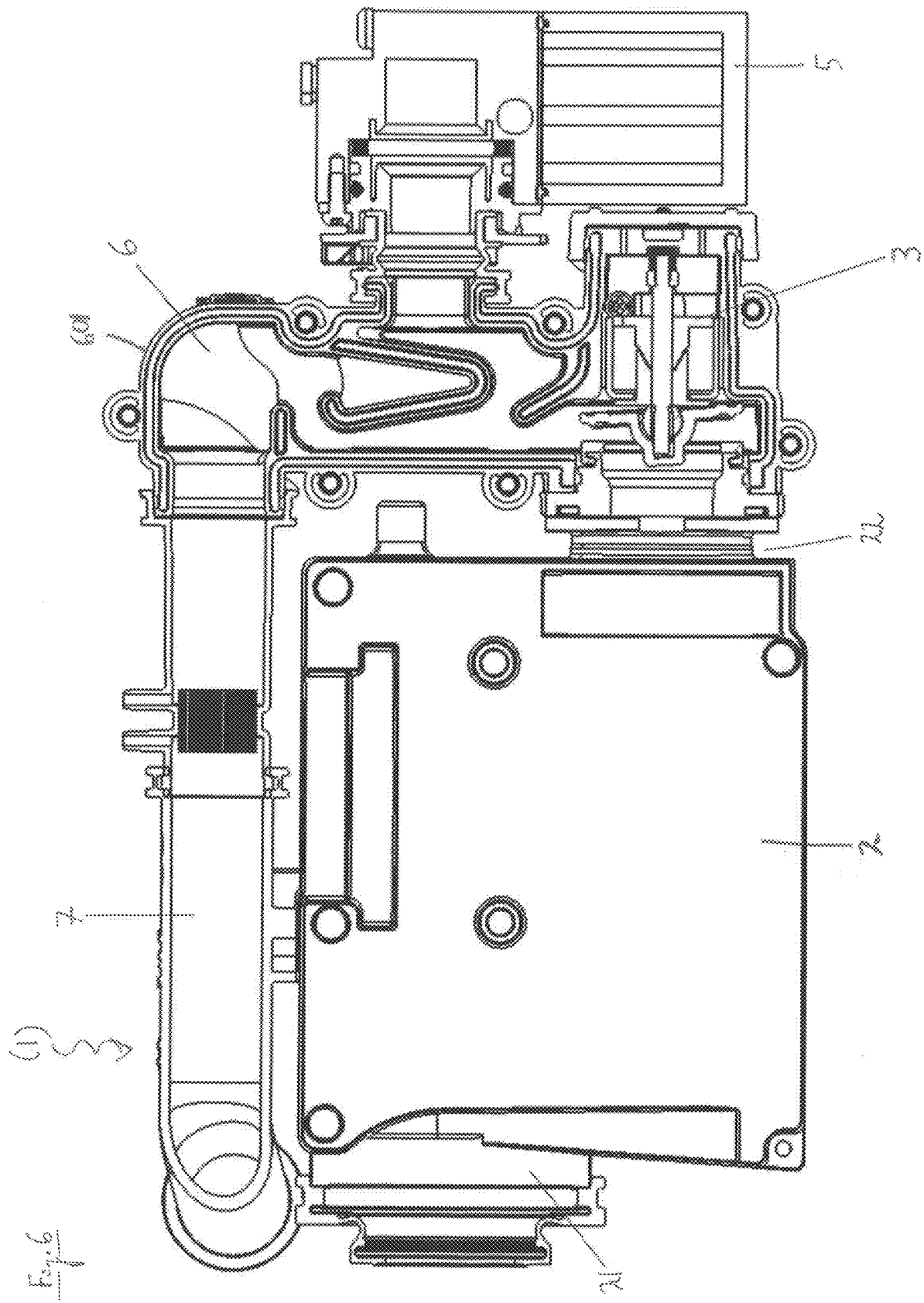

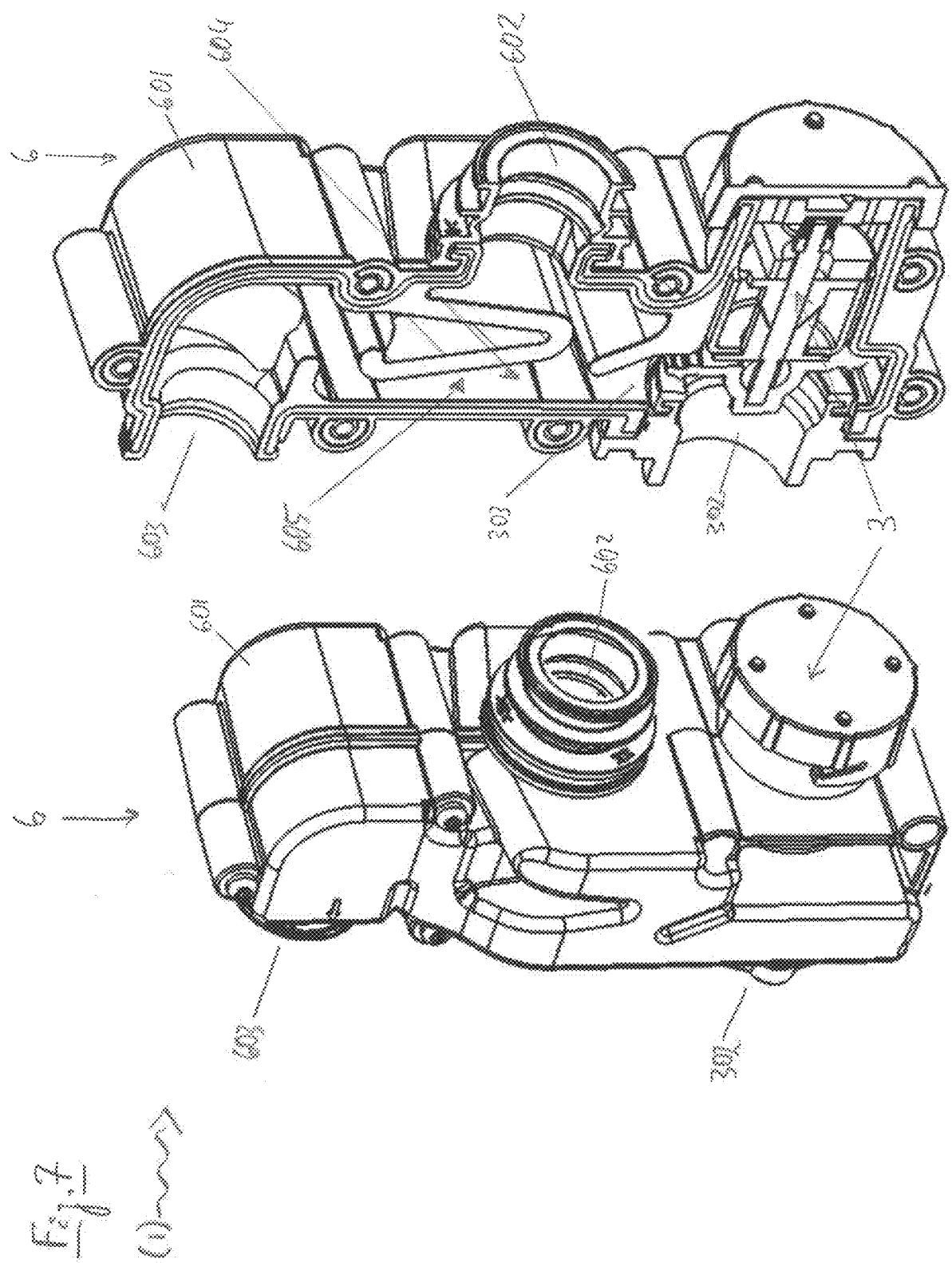

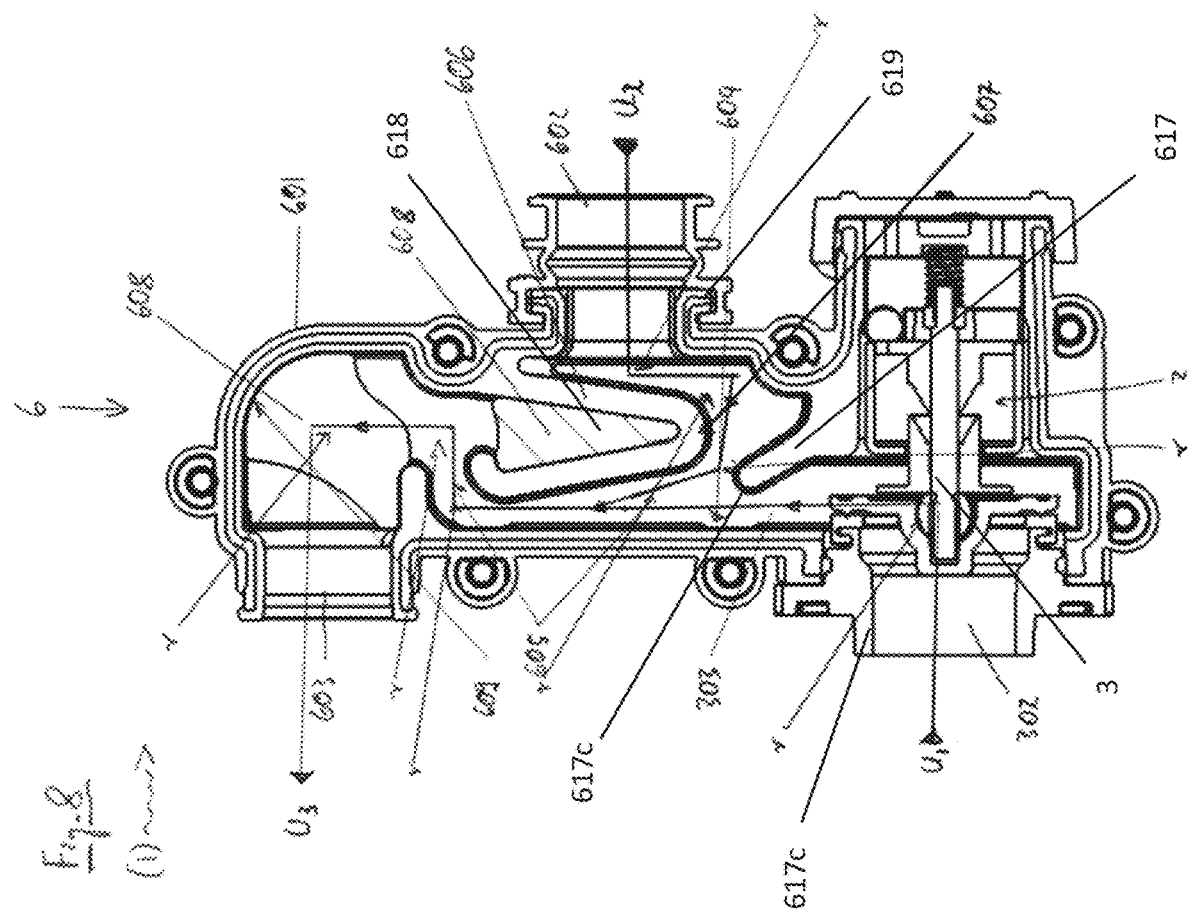

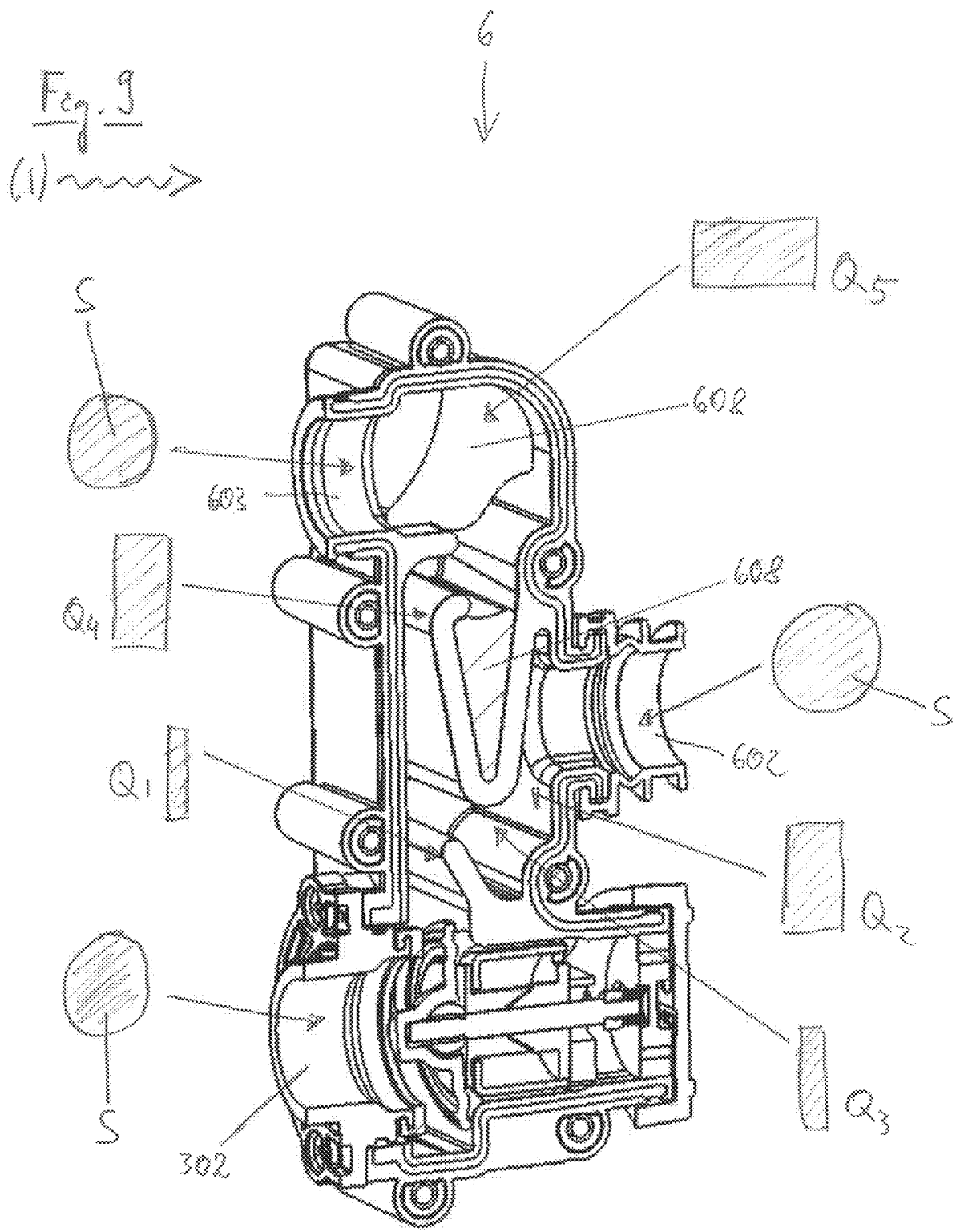

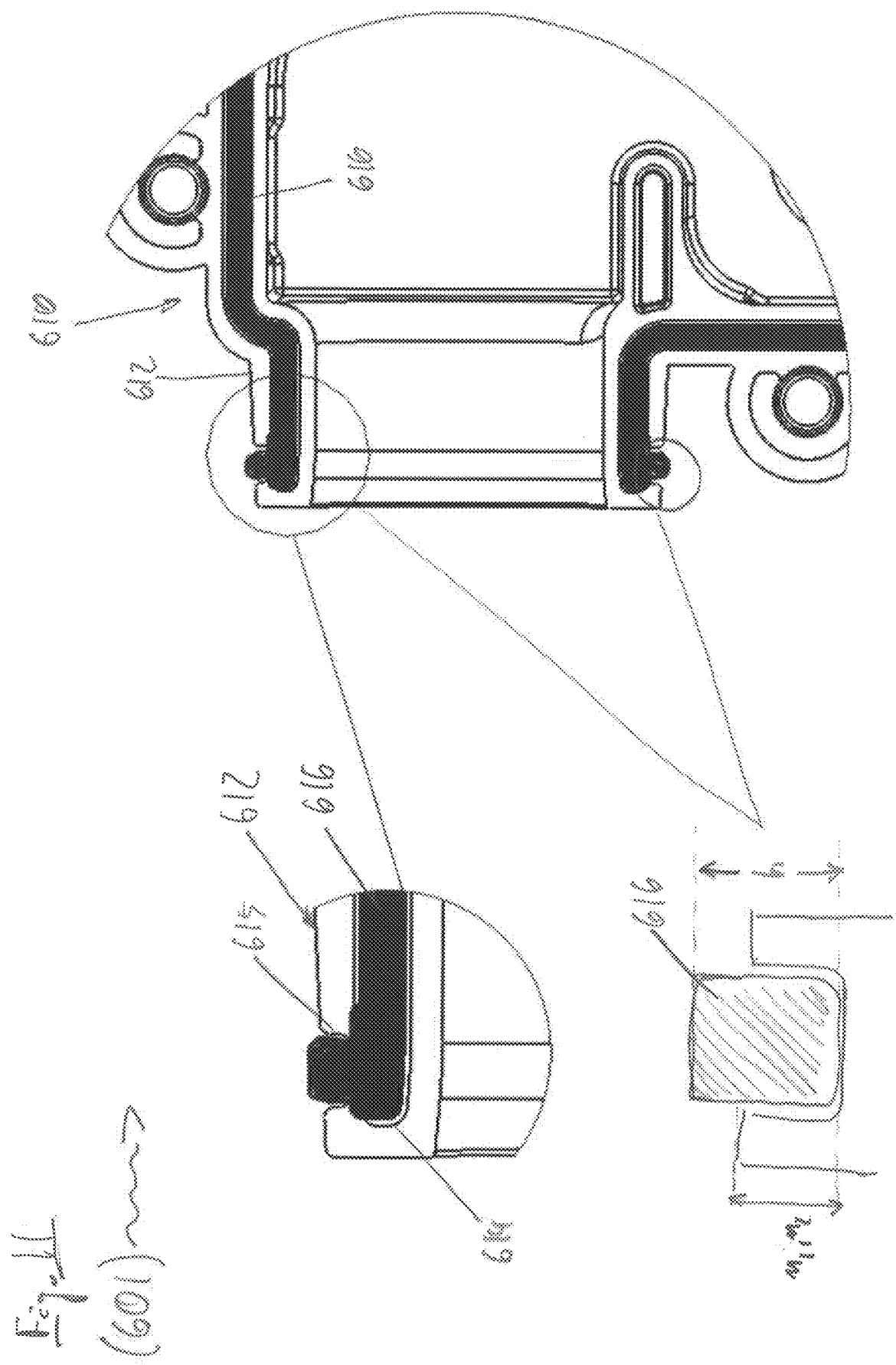

RESPIRATOR WITH A MIXING CHAMBER, AND MIXING CHAMBER FOR A RESPIRATOR

CROSS-REFERENCE TO RELATED APPLICATIONS

The present application is a continuation of patent application Ser. No. 16/808,482, filed Mar. 4, 2020, which claims priority under 35 U.S.C. § 119 of German Patent Application No. 102019001657.2, filed Mar. 7, 2019; the entire disclosures of these two applications are expressly incorporated by reference herein.

BACKGROUND OF THE INVENTION

1. Field of the Invention

The invention relates to a respirator which is provided to support or maintain the respiratory function of a patient and which has an electric fan and/or a valve as respiratory gas source. The patient can in this case be a human or an air-breathing animal, for example a mammal. The invention relates in particular to a respirator in which at least one auxiliary gas is admixed to the delivered respiratory air. The invention further relates to a respirator configured as an anesthesia apparatus.

2. Discussion of Background Information

An important aspect critical to the safety of respirators is that they must ensure the delivery of respiratory gas in the event of a failure of the respiratory gas source. It is a requirement of respirators that the administered gases are mixed in the correct way and that effective sound insulation is provided.

In view of the foregoing, it would be advantageous to have available a respirator that is improved in relation to the prior art.

SUMMARY OF THE INVENTION

The present invention provides a respirator which comprises an electronic control device, and also a pneumatic main line in which the following are pneumatically connected: a respiratory gas source, at least one valve, a mixing chamber, a gas-dosing unit and a supply line. The gas-dosing unit is configured to convey external air and/or oxygen and/or anesthetic gas into the mixing chamber, the respiratory gas source is configured to deliver respiratory gas to the supply line, the mixing chamber is configured to make available respiratory gas, the supply line is configured to supply the patient with respiratory gas, and the at least one valve is configured to at least temporarily reduce a stream of respiratory gas to the patient.

The mixing chamber may be configured to make available respiratory gas by mixing external air and/or oxygen and/or anesthetic gas.

The respiratory gas source may be positioned in the pneumatic main line and may be configured as an electric fan, and a fan output may be connected pneumatically to the valve, and the valve may be connected pneumatically to the mixing chamber, and the mixing chamber may be connected pneumatically both to a gas-dosing unit and to a supply line, the input of the electric fan may be configured to make available external air, wherein the gas-dosing unit may be configured for adjustable pneumatic feeding of an oxygen-containing auxiliary gas in addition to or instead of the delivered external air into the mixing chamber, wherein the supply line may be configured to supply the patient with a respiratory gas consisting of the delivered external air or a gas mixture of the external air and the auxiliary gas or the auxiliary gas alone, wherein the valve may be configured to at least temporarily reduce or interrupt a stream of external air into the mixing chamber.

The valve may be configured as part of the mixing chamber or may be arranged in a common housing of the mixing chamber, wherein the valve in the pneumatic main line may be arranged downstream from the fan output in the direction of flow and upstream from the gas-dosing unit in the direction of flow, wherein the gas-dosing unit may be arranged upstream from the supply line in the direction of flow.

In the direction of flow in the pneumatic main line, the fan output may be connected pneumatically to the valve, the valve may be connected pneumatically to a mixing chamber, and the mixing chamber may be connected pneumatically both to a gas-dosing unit and to a supply line, wherein the suction input may be configured to deliver external air, wherein the gas-dosing unit may be configured for adjustable pneumatic feeding of an oxygen-containing auxiliary gas in addition to or instead of the delivered external air into the mixing chamber, wherein the supply line may be configured to supply the patient with a respiratory gas consisting of the delivered external air or a gas mixture of the external air and the auxiliary gas or the auxiliary gas alone, wherein the control device may be used to adjust the auxiliary gas fraction, the respiration pressure and a respiration flow of the respiratory gas, and wherein the control device may additionally be configured to shut off the valve with simultaneous opening of the gas-dosing unit, and the gas-dosing unit itself may be configured to make available respiratory gas in the event of a failure of the electric fan and/or of the power supply and/or in the event of a failure of the processor and/or in the event of the software crashing.

The mixing chamber may have a port for the gas-dosing unit, a port for the supply line, and a port for the respiratory gas source.

The mixing chamber may have at least one port for connection to a component, wherein the port may have a releasable closure for rapid mounting of the component. The releasable closure may be, for example, a bayonet closure and serves for rapid mounting, positioning and sealing. The mixing chamber may have elements for reducing the airborne noise and elements for mixing the gases. Moreover, the mixing chamber preferably comprises elements which prevent oxygen leakage in the case of oxygen ventilation, and elements which prevent the patient from rebreathing into the respirator.

The valve may have an inlet and an outlet in a valve housing and may be connected pneumatically via the outlet to the suction input or via the inlet to the fan output, wherein the electric fan and the valve may be electronically regulated with the control device in at least one common control circuit, and the control device itself may be electronically regulated and/or automatically regulated at least partially with a processor via an algorithm in the form of software, wherein functional assemblies and optionally measuring and/or regulating instruments may be connected pneumatically in or on the pneumatic main line and/or in further pneumatic branch lines and/or secondary lines and/or return lines, wherein the functional assemblies may be electronically regulated by means of the control device, and the measuring and/or regulating instruments may likewise be optional assemblies of the control device.

The valve may be configured as a nonreturn valve and/or as a solenoid valve and/or as a proportional valve.

The valve is preferably configured as a solenoid valve with an electromagnet fixed in a valve housing and with a magnetically movable valve piston, wherein the valve piston has a sealing plate with a seal, wherein the sealing plate acts on an inlet, and wherein the valve piston is pressed with the sealing plate against the inlet by a spring, such that a gas flow from or to the electric fan is suppressed.

The electromagnet, in the closed state of the solenoid valve, may be currentless.

When current flows through the electromagnet, an adjustable or predetermined magnetic force acts on the magnetically movable valve piston, wherein the magnetically movable valve piston compresses the spring to a predefinable extent, wherein, in an opened state, the magnetic force acting on the magnetically movable valve piston is greater than the spring force.

The control device may comprise at least one processor (or computer) or has several processors, in order to control at least the electric fan, the valve and measuring and/or regulating instruments.

The control device may be configured to automatically shut off the valve in the event of a failure of the electric fan and/or in the event of a failure of the control device.

The claimed respirator may comprise an electronic control device and an electric fan with a suction input and a fan output. The respirator may be configured to deliver respiratory gas or anesthetic gas with the electric fan through a pneumatic main line to a patient, that is to say to supply gas to the patient. The respirator moreover may comprise a valve, wherein the valve itself has a valve housing with an inlet and an outlet. The valve housing as an assembly is gas-tight, except for the inlet and the outlet. Inside the pneumatic main line, the electric fan and the valve are connected pneumatically to each other via the outlet of the valve to the suction input or via the inlet of the valve to the fan output of the electric fan. Thus, in the claimed respirator, a direction of flow of a gas or of a gas mixture is generally fixed from the electric fan to the patient, irrespective of whether the valve is connected pneumatically upstream from the suction input or downstream from the fan output.

The valve may be regulatable electronically. Here, the electric fan and the valve are electronically regulated with the control device in at least one common control circuit, wherein the control device itself can be electronically regulated and/or automatically regulated at least partially with a processor via an algorithm in the form of software. For this purpose, the respirator may have a power supply which is configured to supply all of the electrically operated and electrically and/or electronically controlled apparatus components of the proposed respirator. The power supply may be realized, for example, by an attachment to an electricity supply grid.

In the proposed respirator, the control device may be configured for regulating the gas supply to the patient in respect of the respiration pressure and the respiration flow via the control device. The supply of gas to the patient can be regulated here by regulating the power of the electric fan. In addition or alternatively, the gas may be supplied to the patient by regulation of the valve with the control device, wherein the valve may be configured as a continuously adjustable valve, in particular as a proportional valve.

Moreover, the claimed respirator optionally has flow and/or pressure sensors which may be connected pneumatically in or on the pneumatic main line and/or in further pneumatic branch lines and/or secondary lines and/or return lines of the respirator. The flow and pressure sensors can be electronically controlled by the control device. The flow and/or pressure sensors are thus optional assemblies of the control device and therefore electronically connected to the control device. By way of the pressure or flow values which are measured by the flow and/or pressure sensors and relate to the gas or gas mixture flowing through the pneumatic main line, in particular anesthetic gas or respiratory gas, the electronic control device can be used to set desired or fixed pressure and/or flow values of this gas or gas mixture by regulating the valve and/or by regulating the power of the electric fan.

Compared to conventional respirators that have an electric fan, the respiration pressure and the respiration flow can be set much more precisely with the control device of the proposed respirator. Thus, the proposed respirator has greater operating safety. Moreover, to further improve the operating safety, the valve of the proposed respirator may additionally be configured as a shut-off valve.

In or on the pneumatic main line and/or in further pneumatic branch lines and/or secondary lines and/or return lines, and depending on the intended use of the proposed respirator, it is possible to pneumatically connect further functional assemblies and/or, in addition to the flow and/or pressure sensors, further such measuring and/or regulating instruments, wherein the measuring and/or regulating instruments are likewise optional assemblies of the control device. Such functional assemblies are, for example, a gas-dosing unit, a mixing chamber and a supply line. The gas-dosing unit is configured for pneumatic feeding of gases into the mixing chamber. The mixing chamber is configured for mixing the fed-in gases. The supply line itself is guided via an interface directly to the respiratory organs of the patient, wherein the interface is provided, for example, by a breathing mask or tubing. The functional assemblies are likewise electronically regulated with the control device. In or on the pneumatic main line and/or in further pneumatic branch lines and/or secondary lines and/or return lines, and depending on the purpose of the regulation and/or the intended use, it is optionally also possible here to connect more than just one valve.

In a typical embodiment, the proposed respirator is configured for operation at an operating pressure of at most 1 mbar to 2 mbar with the electric fan opened and with a maximum gas flow of 180 l/min to 200 l/min, wherein the operating pressure and the gas flow can also be adjusted to other values. With the electric fan closed, a pressure increase as far as a limit pressure is limited by the fact that the valve opens when the limit pressure is exceeded. In a typical embodiment of the claimed respirator, the limit pressure is set at 100 mbar, although it is also possible for the valve to be configured for other limit pressures.

Advantageous refinements of the proposed respirator in terms of safety aspects and with respect to its intended use are discussed below.

In a first refinement of the invention, the control device of the proposed respirator is configured to automatically shut off the valve in the event of a failure of the electric fan and/or in the event of a failure of the processor and/or in the event of the software crashing. Thus, in the event of a failure of the processor and/or in the event of the software crashing, dead space ventilation of the patient through the electric fan and a return flow of gases through the fan output into the electric fan are particularly advantageously prevented, if the valve is connected pneumatically upstream from the fan output. If a valve is connected pneumatically upstream from the suction input, passage of gases or external air through this opening of the electric fan is prevented.

In a second refinement, the proposed respirator is configured as an anesthesia apparatus. In the direction of flow in the proposed respirator, a gas-dosing unit is connected pneumatically to a mixing chamber. The mixing chamber is in turn connected pneumatically to the suction input of the electric fan, and the fan output is connected pneumatically to a supply line. Thus, in this sequence of pneumatic connection with respect to the direction of flow, the gas-dosing unit, the mixing chamber, the electric fan and the supply line form the pneumatic main line, wherein the valve is connected pneumatically upstream from the suction input or downstream from the fan output, or valves are each connected pneumatically upstream from the suction input and downstream from the fan output in the pneumatic main line.

If the or a valve is arranged upstream from the suction input, the inlet is connected pneumatically to the mixing chamber, and the outlet is connected pneumatically to the suction input. If the or a valve is arranged downstream from the fan output, the inlet is connected pneumatically to the fan output, and the outlet is connected pneumatically to the supply line.

Here, the gas-dosing unit is configured to pneumatically feed gases and at least one anesthetic agent into the mixing chamber, the mixing chamber is configured to mix an anesthetic gas from the fed-in gases, and the suction input is configured to deliver anesthetic gas. The supply line is configured to supply the patient with anesthetic gas, wherein the anesthetic gas contains oxygen and at least one anesthetic agent. Optionally, in this embodiment of the claimed respirator, a rebreathing system is in addition attached pneumatically on the pneumatic main line, which rebreathing system particularly advantageously permits a return of unused anesthetic agent to the patient while avoiding an emission into the environment.

With the control device, it is possible for gases and at least one anesthetic agent to be fed pneumatically through the gas-dosing unit in such a way as to be adjustable independently of one another in terms of their fractions in the anesthetic gas, that is to say the feeding of each gas and anesthetic agent into the mixing chamber is adjustable independently of the other gases in terms of pressure and/or volume and/or flow. This includes the selection or limitation to one gas or to individual gases and/or anesthetic agents, which are provided for feeding into the mixing chamber. With the control device, it is likewise possible to adjust and thereby regulate the respiration pressure and the respiration flow of the anesthetic gas admixed in the mixing chamber. Preferably, and particularly advantageously, the control device is configured to automatically shut off the valve and in addition to automatically shut off the gas-dosing unit in the event of a failure of the electric fan and/or of the power supply and/or in the event of a failure of the processor and/or in the event of the software crashing.

In a third refinement, which is complementary to the second refinement, the proposed respirator is configured exclusively for supplying a patient with respiratory gas. In the direction of flow in this embodiment, the fan output is connected pneumatically to the valve. The outlet of the valve is in turn connected pneumatically to a mixing chamber, wherein the mixing chamber is connected pneumatically both to a gas-dosing unit and to a supply line. Moreover, in this embodiment of the proposed respirator, the supply line, as described at the outset, is guided to the respiratory organs of the patient. Thus, in this embodiment of the proposed respirator, in the sequence of pneumatic connection with respect to the direction of flow, the suction input, the fan output to the valve, the outlet of the valve to the mixing chamber and the mixing chamber both to a gas-dosing unit and to the supply line form the pneumatic main line.

Here, the suction input is configured to deliver external air, and the gas-dosing unit is configured for adjustable pneumatic feeding of an oxygen-containing auxiliary gas in addition to or instead of the delivered external air into the mixing chamber. The supply line is configured to supply the patient with a respiratory gas consisting of the delivered external air or a gas mixture of the external air and the auxiliary gas or the auxiliary gas alone. The control device can be used to adjust the auxiliary gas fraction, the respiration pressure and a respiration flow of the respiratory gas.

Here, the control device is configured to automatically shut off the valve, and in addition to automatically shut off the valve with simultaneous opening of the gas-dosing unit, in the event of a failure of the electric fan and/or of the power supply and/or in the event of a failure of the processor and/or in the event of the software crashing.

In the event of a failure of the electric fan and/or of the power supply and/or in the event of a failure of the processor and/or in the event of the software crashing, the gas-dosing unit is configured for the fully automatic and/or partially assisted ventilation of the patient. For this purpose, the gas-dosing unit has an electronic back-up control device independent of the control device, and a back-up power supply independent of the power supply. In the event of at least one of the aforementioned failures occurring, both the back-up control device and the back-up power supply are configured to automatically switch on and supply the gas-dosing unit with electric current. Here, the electric fan, the valve and also the gas-dosing unit are electronically regulated with the back-up control device in at least one common control circuit, wherein the back-up control device itself can likewise be electronically regulated and/or automatically regulated at least partially with a processor via an algorithm in the form of software. The back-up power supply is formed, for example, by accumulators.

Advantageous variants of the valve of the claimed respirator are described in more detail below.

In a first preferred variant, the valve is directly controlled. For this purpose, the valve has a lifting electromagnet, which is fixed in the valve housing and which has a magnetically attractable valve piston, wherein the valve piston is mounted linearly in the lifting electromagnet. The valve piston is produced from a magnetically attractable material, for example from iron or an iron alloy, and/or is itself formed as a permanent magnet. The valve piston is displaceable on a geometric longitudinal axis in the lifting electromagnet by means of an electric current, wherein a restoring spring in the valve housing is braced at one end with the valve piston. The restoring spring has a restoring force parallel to the longitudinal axis. The restoring spring is thus expandable in the direction of the longitudinal axis, wherein, with the lifting electromagnet switched on electrically, a force exerted by the valve piston can be set to be greater than the restoring force.

By current regulation at the lifting magnet, the valve can thus be operated optionally as a proportional valve. This particularly advantageously permits precise setting and/or readjustment of fixed pressure and/or flow values of the anesthetic gas or of the respiratory gas.

A sealing plate is mounted vertically on the front of the valve piston. The sealing plate is electrically displaceable by the valve piston on the common geometric longitudinal axis. The inlet is configured as a valve seat, wherein the sealing plate for this purpose is arranged on the inlet opposite an elastic flange seal.

In the closed state of the valve, wherein the lifting electromagnet is currentless, the sealing plate is pressed onto the flange seal by the restoring force of the restoring spring. Thus, in this state of connection, the inlet is sealed off by the flange seal. The sealing plate is additionally given mechanical play, for example via a ball joint, with three degrees of freedom. Only in this way is it possible to ensure secure sealing, in the currentless state of the electromagnet, by compensation of a production-related angle tolerance of the valve. The mechanical play is realized, for example, by a ball socket applied to the sealing plate, wherein the ball socket is latched onto a ball on the valve piston. Optionally, a circumferential sealing edge is applied to the sealing plate, wherein the sealing edge is pressed together with the sealing plate onto the flange seal in the closed state of the valve, and the sealing is in this way reinforced particularly advantageously.

The flange seal is produced from an elastic material, for example silicone or butadiene rubber. By contrast, the sealing plate is produced from a hard or elastic material, for example from metal or ABS or silicone or rubber.

Preferably, the claimed respirator is constructed in such a way that, in the direction of flow to the patient, a laminar stream of the gas flow in the pneumatic line is obtained. The better a laminar stream is formed, that is to say the less the flow turbulence, the more precisely the gas pressure and the gas flow can be measured and adjusted.

For this purpose, that is to say in order to prevent flow turbulence, the inlet and also the outlet each have an identical cross section of flow with respect to surface area. During the operation of the claimed respirator and in the opened state of the valve, a gas flow is permitted both on the side of the sealing plate facing toward the inlet and also to the rear thereof, by means of free spaces being provided for inflowing gas around the electromagnet and inside the valve housing. During the operation of the claimed respirator and in the opened state of the valve, the mathematical product of the circumference of the sealing plate and the distance between the sealing plate and the edge of the inlet formed by the flange seal thus moreover corresponds to the cross section of flow with a deviation of not more than 20%. During optimal operation of the valve as a proportional valve, the distance between the sealing plate and the edge of the inlet is adjustable.

The inlet, the valve housing, the lifting electromagnet, the sealing plate, together with the optional sealing edge, and the flange seal are preferably produced to be rotationally symmetrical with respect to the longitudinal axis. The compensation of the production-related angle tolerance of the valve is optimized in this way. This is also more advantageous for achieving the laminar stream.

In a second preferred variant, the valve is configured as a nonreturn valve for shutting off the electric fan in the event of a failure of the power supply and/or in the event of the outlet having an overpressure relative to the inlet.

Developments of the proposed respirator with respect to the mixing chamber are described below, wherein the respirator is configured exclusively to supply a patient with respiratory gas. Here, the valve of the claimed respirator is optionally configured in its above-described first preferred variant and/or second preferred variant.

In such a first development with respect to the mixing chamber, the mixing chamber is configured as a valve housing, and the valve is thus integrated in the mixing chamber. Here, the inlet of the valve is configured as a pneumatic inlet to the mixing chamber, and the outlet is guided pneumatically into an inner chamber of the mixing chamber. The inner chamber is connected pneumatically to the gas-dosing unit via a port and to the supply line via a further port. In this way, a compact structure of the claimed respirator is achieved in a particularly advantageous manner.

Preferably, the cross section of flow of the inlet of the valve, in respect of surface area and also geometry, is identical to the respective cross section of flow both of the port for the gas-dosing unit and of the port for the supply line. In this way, the laminar stream through the mixing chamber is achieved particularly advantageously.

Tests carried out even with sound-insulated electric fans have shown that, on account of vibrations being transmitted, especially through the gas flow, to functional assemblies arranged in the pneumatic main line on the side of the fan output, the functional assemblies have a higher noise generation than the electric fan itself. In particular, a more important contribution to undesired noise generation is made through the operation of a gas-dosing unit.

Therefore, the inner chamber optionally has in addition a labyrinth for attenuating the noise generated by the operation of the electric fan and the gas-dosing unit. It has surprisingly been found that much less acoustic insulation can be obtained with perforated plates than with a labyrinth.

In a second development of the proposed respirator with respect to the mixing chamber, the flow of the delivered external air and/or the flow of the fed-in auxiliary gas and/or the flow of the respiratory gas in each case additionally have at least once a deflection in the labyrinth. This particularly advantageously brings about a reflection of the sound waves generated by the electric fan.

Alternatively or in addition, the flow of the delivered external air and/or the flow of the fed-in auxiliary gas and/or the flow of the respiratory gas in each case have at least once a change of the flow cross section vertically with respect to the direction of flow in the labyrinth. This second development corresponds to an improvement of the design features of the labyrinth in terms of sound insulation.

In a third development of the proposed respirator with respect to the mixing chamber, the mixing chamber upstream from the port of the gas-dosing unit has a deflection wedge with a wedge tip, wherein the flow of the fed-in oxygen is routed around the wedge tip. Here, the deflection wedge is configured with a hollow shape or has a filler composed of foam. The deflection wedge provides a coming together of the flow of the delivered external air with the flow of the auxiliary gas fed in to the flow of the respiratory gas, which results in better mixing. Preferably, the narrowing at the stump of the deflection wedge to the inner wall of the inner chamber is chosen sufficiently great to ensure that a compression, that is to say pressure increase, of the gas flow is no longer measurable. If the deflection wedge has a hollow shape, this particularly advantageously permits a refraction of the sound waves generated by the electric fan and the gas-dosing unit and hence an acoustic damping.

The damping of the sound waves is additionally improved by the fact that the deflection wedge is filled with foam. A further improvement of the acoustic damping is obtained if the claimed respirator additionally has the features of the second development of the proposed respirator with respect to the mixing chamber.

In a fourth development of the proposed respirator with respect to the mixing chamber, the labyrinth has a surface which is at least partially lined with macroporous foam. In this way, and in particular additionally in combination with at least one of the features of the first to third developments of the proposed respirator with respect to the mixing chamber, further optimization of the acoustic damping can be achieved.

In this fourth development of the proposed respirator with respect to the mixing chamber, the surface in the labyrinth alternatively or additionally has antimicrobial properties at least in subregions, wherein the foam itself optionally has antimicrobial properties. For this purpose, for example, the mixing chamber is produced from a plastic, for example polystyrene (PS) or ABS, to which, for example, silver zeolite or silver particles are added. Analogously to this, biocidal silver additives, for example, are added to the foam. Alternatively, the surface of the labyrinth and/or the foam have an antimicrobial surface coating which, for example, contains silver and/or other biocidal metals and/or chemical compounds thereof and/or biocidal quaternary ammonium and/or phosphonium salts. Therefore, in the event that a patient undergoing treatment rebreathes through the supply line, the risk of contamination of the mixing chamber with microbes is particularly advantageously averted, which situation would otherwise cause infection of subsequently treated patients.

The mixing chamber of the proposed respirator, which is configured exclusively for supplying respiratory gas to a patient, is assembled for example from a construction piece and a mating piece to form a structural part. The construction piece and the mating piece are produced independently of each other from an identical or different non-elastic material. The construction piece and the mating piece are preferably produced cost-effectively from a thermoplastic, for example ABS, by means of injection molding. The construction piece and the mating piece each have connecting edges that engage each other with a form fit.

The mixing chamber may also be characterized in that the mixing chamber has a mixing chamber housing which has a port for the gas-dosing unit, a port for the supply line, and a port for the respiratory gas source.

The mixing chamber may also be characterized in that the mixing chamber has a structural part, for example a mixing chamber housing, which is produced from a construction piece and a mating piece by form-fit and force-fit engagement, wherein the construction piece and the mating piece each have connecting edges that engage each other with a form fit, wherein, in the construction piece, a groove is let at least into a connecting edge and runs parallel to the length of the connecting edge, and a transverse groove is let in which opens vertically into the groove and interrupts the associated connecting edge, wherein an elastic and compressible one-piece flat seal is introduced extending both in the groove and in the transverse groove, wherein the flat seal has a form-fit match both to the groove and to the transverse groove, wherein the flat seal is given a sealing height greater than the depth of the groove and the depth of the transverse groove and corresponding at most to twice the depth of the groove and twice the depth of the transverse groove, and wherein the flat seal is configured protruding above the transverse groove through the connecting edge by not more than twice the depth of the transverse groove.

The connecting edge or connecting edges of the construction piece each have a continuous groove along the entire length of the connecting edge. A flat seal with a form-fit match to the groove is introduced into each groove with a groove depth, for example by injection of a plastic. The flat seal is produced from an elastic material, for example silicone or butadiene rubber. The flat seal has a sealing height that is greater than the groove depth.

The construction piece and the mating piece are connected to each other by form-fit and force-fit engagement, with the flat seal lying on the inside. The force-fit connection is provided, for example, by screwing. Here, sealing of the mixing chamber is achieved by the respective flat seal being pressed into the respective groove of the construction piece and onto the connecting edge of the mating piece.

In this structural part produced from the construction piece and the mating piece, the design is additionally such that the openings for the supply line and the inlet are divided by respective connecting edges of the construction piece and of the mating piece. According to previous teaching in manufacturing technology, such designs are generally to be avoided since, according to the prior art, they inevitably lead to leaks at the openings in question, for example at the opening for the supply line and for the inlet. Leaks are also unavoidable starting from a specific length of the connecting edge.

However, this problem can be solved by the fact that the construction piece and the mating piece each have connecting edges that engage each other with a form fit, wherein, in the construction piece, a groove is let at least into a connecting edge and runs parallel to the length of the connecting edge, and a transverse groove is let in which opens vertically into the groove and interrupts the associated connecting edge. The transverse groove is let into the associated connecting edge at the location of the latter where, otherwise, a leak potentially or actually occurs after force-fit engagement.

Moreover, for sealing purposes, an elastic and compressible one-piece flat seal is introduced extending both in the groove and in the transverse groove, wherein the flat seal has a form-fit match both to the groove and to the transverse groove, that is to say the flat seal is configured extending over the entire groove and over the entire transverse groove. The flat seal is given a sealing height greater than the depth of the groove and the depth of the transverse groove and corresponding at most to twice the depth of the groove and twice the depth of the transverse groove. The flat seal is configured protruding above the transverse groove through the connecting edge by not more than twice the depth of the transverse groove. By compression of the flat seal in the transverse groove, through form-fit and force-fit engagement to form the structural part, the sealing is reinforced at the respective location of the connecting edge.

This solution to a problem of manufacturing technology is applicable to any desired structural part produced from any desired number of construction pieces and mating pieces by form-fit and force-fit engagement. The production of the construction pieces, of the mating pieces and of the flat seals is not in any way limited to plastics. For example, the construction pieces and the mating pieces are produced from steel and the flat seals from copper.

BRIEF DESCRIPTION OF THE DRAWINGS

The proposed respirator is explained in more detail below with reference to a drawings, in which:

FIG. 1 shows the claimed respirator 1, which is configured as an anesthesia apparatus;

FIG. 2 shows the claimed respirator 1, which is configured to ventilate a patient with respiratory gas;

FIG. 3 shows a plan view of a valve 3 of the respirator 1;

FIG. 4 shows a cross section through the valve 3 in the closed state;

FIG. 5 shows a cross section through the solenoid valve 3 in the opened state;

FIG. 6 shows a partially sectioned side view of the respirator 1, which is configured to ventilate a patient with respiratory gas and has a mixing chamber 6 in which the solenoid valve 3 is integrated;

FIG. 7 shows an oblique view of the mixing chamber 6 in which the valve 3 is integrated, in a closed form on the left and in cross section on the right;

FIG. 8 shows a cross section of the side view of the mixing chamber 6, in which the valve 3 is integrated, and illustrates deflections r;

FIG. 9 shows a sectioned oblique view of the mixing chamber 6, in which the valve 3 is integrated, and illustrates changes of a respective flow cross section $Q_1$, $Q_2$, $Q_3$, $Q_4$ and $Q_5$;

FIG. 11 shows a plan view of a connecting edge 612 of the construction piece 610, illustrating the connecting edge 612 with a groove 614, a transverse groove 615 and a flat seal 616.

DETAILED DESCRIPTION OF EXEMPLARY EMBODIMENTS OF THE INVENTION

Figure 10:
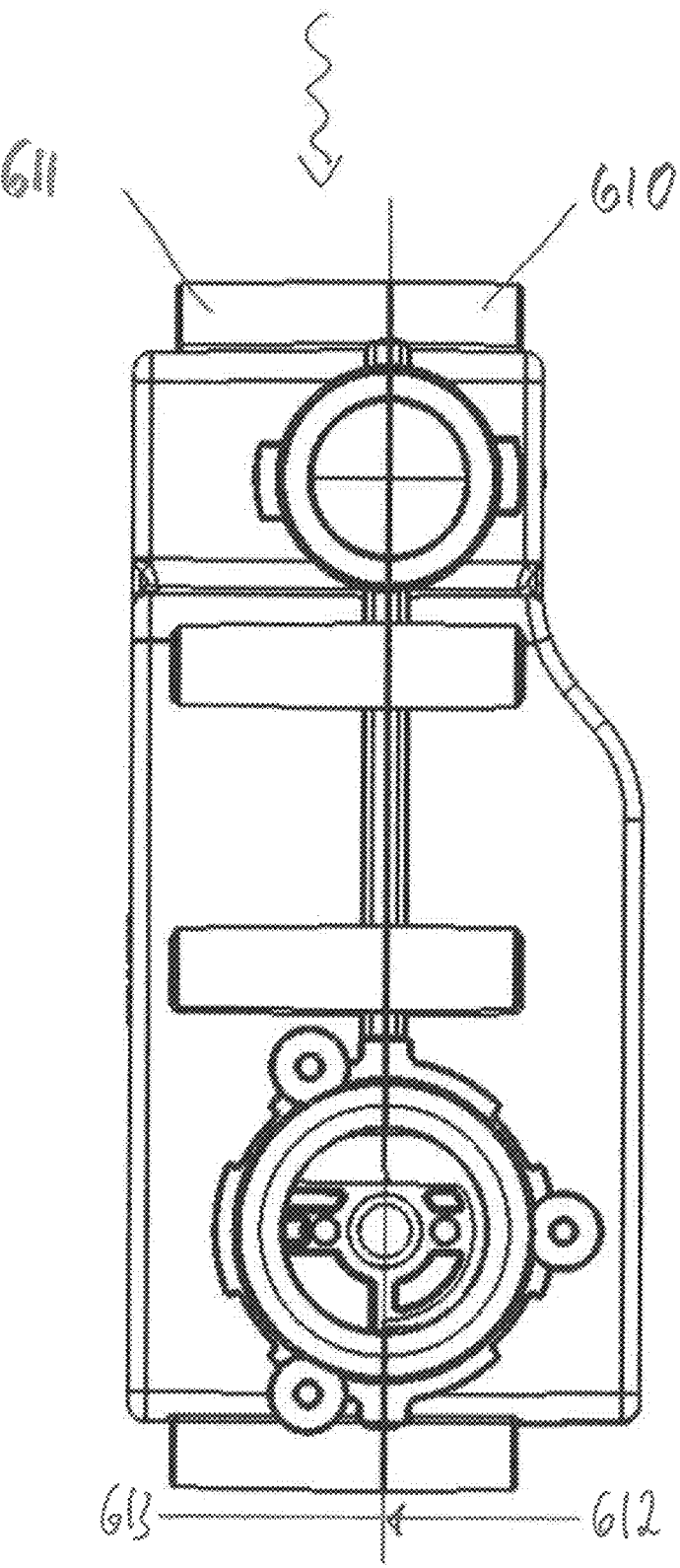
FIG. 10 shows a side view of a structural part 601 produced by form-fit and force-fit engagement, for example a mixing chamber housing 601, composed of a construction piece 610 and a mating piece 611.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

In the illustrative embodiments below, the respirator 1 has an electronic control device and an electric fan 2 with a suction input 21 and a fan output 22. The respirator is configured to deliver respiratory gas or anesthetic gas with the electric fan 2 to the respiratory organs of a patient, that is to say to supply gas to the patient.

The respirator moreover has a valve 3, wherein the valve 3 itself has a valve housing 301 with an inlet 302 and an outlet 303. In the illustrative embodiments below, the electric fan 2 and the valve 3 are electronically regulated by the control device. The electric fan 2 is connected pneumatically to the valve 3 in a pneumatic main line 4. In the claimed respirator 1, a direction of flow d of a gas or of a gas mixture from the electric fan 2 to the patient is generally fixed.

In the illustrative embodiments below, the control device itself can be electronically regulated and/or automatically regulated with a processor via an algorithm in the form of software. For this purpose, the respirator 1 has a power supply which is configured to supply all of the electrically operated and electrically and/or electronically controlled apparatus components of the proposed respirator. The power supply is realized by an attachment an electricity supply grid.

In the following illustrative embodiments of the respirator, the control device is configured to regulate the gas supply to the patient in terms of the respiration pressure and the respiration flow via the control device. The supply of gas to the patient is regulated here by regulating the power of the electric fan. Moreover, the claimed respirator has flow and/or pressure sensors which are pneumatically connected in or on the pneumatic main line of the respirator. The flow and pressure sensors can be electronically controlled by the control device and are electronically connected to the control device.

According to the invention, the respirator is a CPAP or APAP or BiLevel or home respirator or a clinical respirator or an anesthetic respirator. According to the invention, the valve is configured as a pneumatically or electronically controlled solenoid valve or nonreturn valve or proportional valve.

In the illustrative embodiments below, the valve 3 can also be directly controlled and configured as a nonreturn valve. For this purpose, the control device of the proposed respirator is configured to automatically shut off the valve 3 in the event of a failure of the electric fan 2 and/or in the event of a failure of the processor and/or in the event of the software crashing.

FIGS. 1 to 9 do not show the control device, the processor, the power supply, the flow and pressure sensors, the patient and the respiratory organs of the latter.

In the illustrative embodiments below, the respirator has a gas-dosing unit 5, a mixing chamber 6 and a supply line 7. The supply line 7 itself is guided directly to the respiratory organs of the patient via a hose and/or tubing. FIGS. 1 to 9 do not show the tubing either. FIG. 1, FIG. 2 and FIG. 6 show the different pneumatic circuit diagrams of the pneumatic main line 4 for each of these two different illustrative embodiments.

FIG. 1 shows the claimed respirator 1 which, for example, is configured to supply an anesthetic gas to a patient. In the direction of flow d, illustrated by an arrow, the gas-dosing unit 5 is connected pneumatically to the mixing chamber 6. The mixing chamber 6 is in turn connected pneumatically to the inlet 302, and the outlet 303 of the valve 3 is connected pneumatically to the suction input 21 of the electric fan 2. The fan output 22 is connected pneumatically to the supply line 7. Thus, in this sequence of pneumatic connection in a row and with respect to the direction of flow d, the gas-dosing unit 5, the mixing chamber 6, the valve 3, the electric fan 2 and the supply line form the pneumatic main line 4. The gas-dosing unit 5 is configured for pneumatic feeding of external air, oxygen and nitrous oxide into the mixing chamber 6, the mixing chamber 6 is configured for mixing an anesthetic gas from these fed-in gases, and the suction input 21 is configured to deliver anesthetic gas. The anesthetic gas is thus composed of external air, oxygen and nitrous oxide. The gas-dosing unit 5 thus has a feed input for external air 51, a feed input for oxygen 52 and a feed input for anesthetic gas (nitrous oxide) 53, wherein oxygen and nitrous oxide are delivered from compressed-gas cylinders. The compressed-gas cylinders are not shown in FIG. 1. The supply line 7 is configured to supply the patient with respiratory gas, e.g. anesthetic gas. The control device 8 can be used to adjust the pneumatic feed of these gases independently of each other in terms of their quantities and to adjust the respiration pressure and a respiration flow of the anesthetic gas. The control device 8 is additionally configured to automatically shut off the gas-dosing unit in the event of a failure of the electric fan 2 and/or of the power supply and/or in the event of a failure of the processor and/or in the event of the software crashing. A pneumatic return line is attached to the pneumatic main line 4, wherein the pneumatic return line is configured to return anesthetic gas to the pneumatic main line 4. The pneumatic return line is not shown in FIG. 1.

FIG. 2 shows the claimed respirator 1, which as a second illustrative embodiment is configured to ventilate a patient with respiratory gas. In the pneumatic main line 4 here by contrast, in the direction of flow d, again illustrated by an arrow, the fan output 22 is connected pneumatically to the valve 3, the valve 3 is connected pneumatically to the mixing chamber, and the mixing chamber 6 is connected pneumatically both to the gas-dosing unit 5 and to the supply line 7. The suction input 21 is configured to deliver external air. The gas-dosing unit 5 is configured for adjustable pneumatic feeding of oxygen as auxiliary gas in addition to or instead of the delivered external air into the mixing chamber 6. Therefore, the gas-dosing unit 5 here has only one feed input for oxygen 52, wherein the oxygen is again delivered via a compressed-gas cylinder. The compressed-gas cylinder is not shown in FIG. 2. The supply line 7 is configured to supply with patient with the respiratory gas consisting of the delivered external air or a gas mixture of the external air and oxygen or pure oxygen. The control device 8 can be used to adjust the oxygen fraction, the respiration pressure and a respiration flow of the respiratory gas. In this second illustrative embodiment, the control device 8 is additionally configured to automatically shut off the valve 3 with simultaneous opening of the gas-dosing unit 5, and the gas-dosing unit 5 itself is configured for fully automatic and/or partially assisted ventilation of the patient in the event of a failure of the electric fan 2 and/or of the power supply and/or in the event of a failure of the processor and/or in the event of the software crashing. For this purpose, the gas-dosing unit 5 has, for example, a separate and independent control device 8, and a separate power supply in the form of accumulators. The separate and independent control device 8 and the accumulators are not shown in FIG. 2.

FIG. 3 shows a plan view of a valve 3 of the claimed respirator 1, which is configured for example for the first two illustrative embodiments as a valve or solenoid valve or nonreturn valve or proportional valve. The valve housing 301 as an assembly is gas-tight, except for the inlet 302 and the outlet 303. The direction of flow d through the inlet 302 and from the outlet 303 is again illustrated by an arrow in the drawing. Both the inlet 302 and the outlet 303 have a cross section of flow S that is identical both in terms of surface area and geometry. In this way, a laminar stream is ensured while at the same time preventing flow turbulence. FIG. 3 does not show any other structural parts of the valve 3; these structural parts are enclosed by the valve housing 301.

The opening cross section of the valve is at least about 180 mm$^2$ and preferably around 230 mm$^2$.

FIG. 4 shows a cross section through the valve 3 of the respirator 1 from FIG. 3 in the closed state. Here, the valve is an electrically connected valve with a magnet. In the closed state, the solenoid valve 3 is connected free of current. The solenoid valve 3 has a lifting electromagnet 304, which is fixed in the valve housing 301 and which has a magnetically attractable valve piston 305, wherein the valve piston 305 is mounted linearly in the lifting electromagnet 304. The valve piston 305 is here produced from nickel steel. The valve piston 305 is displaceable on a geometric longitudinal axis 1 in the lifting electromagnet 304 by means of an electric current, wherein a restoring spring 306 in the valve housing 301 is braced at one end with the valve piston 305. The restoring spring 306 has a restoring force parallel to the longitudinal axis 1. The restoring spring 306 is thus expandable in the direction of the longitudinal axis 1, wherein, with the lifting electromagnet 304 electrically switched on, a force exerted by the valve piston 305 can be set to be greater than the restoring force. By way of a ball 307 screwed onto the valve piston 305, a sealing plate 308 is latched vertically on the front of the valve piston 305, for which reason the sealing plate 308 has a ball socket 309. The sealing plate 308 moreover has a circumferential sealing edge 310, wherein here the sealing plate 308 is produced in one piece with the ball socket 309 and the sealing edge 310 by means of injection molding from ABS. The ball 307 and the ball socket 309 thus form a ball joint 311. The sealing plate 308 is electrically displaceable on the longitudinal axis 1 with the valve piston 305 so as to open the solenoid valve 3. The inlet 302 is thus configured as a valve seat 312, wherein the sealing plate 308 is arranged on the inlet 302 opposite an elastic flange seal 313. The flange seal 313 is produced here from silicone. In the closed state of the solenoid valve 3, in which the lifting electromagnet 304 is currentless, the sealing plate 308 together with the sealing edge 310 is pressed onto the flange seal 313 by the restoring spring 306. By way of the ball joint 311, the sealing plate 308 is additionally given a mechanical play with three degrees of freedom. Thus, in this closed and currentless state, the inlet 302 is also sealed off particularly securely by the flange seal 313, by virtue of the fact that the mechanical play additionally ensures a compensation of production-related angle tolerance of the solenoid valve 3. The inlet 302, the valve housing 301, the lifting electromagnet 304, the valve piston 305, the sealing plate 308, together with the sealing edge 310, and the flange seal 313 are produced with rotational symmetry in relation to the longitudinal axis 1. The compensation of the production-related angle tolerance of the solenoid valve 3 is optimized in this way.

FIG. 5 shows a cross section through the solenoid valve 3 of the respirator 1 from FIG. 4 in the opened state. In the opened state, an electric current is connected at the electromagnet 304. In order to illustrate the mechanical play afforded to the sealing plate 308, the drawing here shows the sealing plate 308 with a lateral inclination. This view corresponds to a theoretical state without gas flow. During the operation of the claimed respirator 1 and in the opened state of the solenoid valve 3, a gas flow is permitted both on the side of the sealing plate 308 facing toward the inlet 302 and also to the rear thereof, by means of free spaces 314 being provided for inflowing gas around the lifting electromagnet 304 and inside the valve housing 301. During the operation of the claimed respirator 1 and in the opened state of the solenoid valve 3, the mathematical product of the circumference of the sealing plate and the distance a between the sealing plate 308 and the edge 315 of the inlet 302 formed by the flange seal 313 thus corresponds to the cross section of flow S. By means of these design features, the laminar stream of a gas flow through the solenoid valve 3 is ensured without flow turbulence.

The valve is configured as a solenoid valve 3 with an electromagnet 304 fixed in a valve housing 301 and with a magnetically movable valve piston 305. The valve piston 305 has a sealing plate 308 with a seal, wherein the sealing plate 308 acts on the inlet 302, i.e. can shut off a gas flow from the electric fan. The valve piston 305 is pressed with the sealing plate 308 against the inlet 302, 312 by a spring 306, such that a gas flow from or to the electric fan is suppressed. In the closed state of the solenoid valve 3, the lifting electromagnet 304 is currentless.

When current flows through the electromagnet 304, an adjustable or predetermined magnetic force acts on the magnetically movable valve piston 305. The magnetically movable valve piston 305 then compresses the spring 306 to a predefinable extent. In an opened state, the magnetic force acting on the magnetically movable valve piston 305 is greater than the spring force.

In the closed state of the solenoid valve 3, the lifting electromagnet 304 is currentless, and the sealing plate 308 together with the sealing edge 310 is pressed onto the flange seal 313 by the restoring spring 306.

The inlet 302 is thus configured as a valve seat 312, wherein the sealing plate 308 is arranged on the inlet 302 opposite an elastic flange seal 313.

The restoring spring 306 is thus expandable in the direction of the longitudinal axis 1, wherein, with the lifting electromagnet 304 electrically switched on, a force exerted by the valve piston 305 can be set to be greater than the restoring force.

The opening cross section of the valve is at least about 180 mm² and preferably around 230 mm².

This configuration has the advantage that, in the event of a power outage or a defect, the valve automatically closes and no energy has to be expended for the closed position.

FIG. 6 shows a partially sectioned side view of the respirator 1 which, analogously to the second illustrative embodiment, is configured to ventilate a patient with respiratory gas but which, as third illustrative embodiment, has a mixing chamber 6 in which the valve 3 is integrated. The mixing chamber thus has a mixing chamber housing 601 which, in terms of its function, also corresponds to the valve housing 301. In FIG. 6, the pneumatic main line 4 is again shown as a detail of the respirator 1. The respirator 1 in this third illustrative embodiment is characterized by a particularly compact structure.

FIG. 7 shows an oblique view of the mixing chamber 6 of the third illustrative embodiment in which the valve 3 is integrated, in a closed form on the left and in cross section on the right. In its mixing chamber housing 601 otherwise produced to be gas-tight, the mixing chamber 6 has, as openings, the inlet 302 of the valve 3, a port 602 for the gas-dosing unit 5, and a port 603 for the supply line 7. The mixing chamber housing 601 is produced by screwing and/or form-fit engagement. The mixing chamber housing 601 has an inner chamber 604 with a labyrinth 605. In this illustrative embodiment, the mixing chamber 6 is made in one piece with the labyrinth 605, e.g. from ABS. The outlet 303 of the valve 3 is guided directly into the inner chamber 604, wherein the outlet 303, in terms of surface area, again has the same cross section of flow S as the inlet 302 and differs only in terms of geometry. Otherwise, the valve 3 is structurally identical to the one shown in FIGS. 3 to 5. Therefore, in this embodiment too, a laminar stream is ensured in a gas flow through the valve 3. In FIG. 7, the valve 3 is shown closed.

FIG. 8 shows a cross section of the side view of the mixing chamber 6 of the third illustrative embodiment, in which the valve 3 is integrated, and illustrates deflections r of gas flows. The inner chamber 604 of the mixing chamber 6 has, upstream from the port 602 for the gas-dosing unit 5, a deflection wedge 606 with a wedge tip 607. The deflection wedge 606 can here be embodied as a constituent part of the labyrinth 605. The deflection wedge 606 forms a cul-de-sac 618 for the flow path. The cul-de-sac 618 is a structural trap region for resonances. For the sound waves, this region, which is for example filled completely with insulating material 608, serves as a resonance basin and trap basin for sound waves, which are "trapped" therein and thus damp the sound.

A filling of insulating material, for example macroporous foam 608, is for example introduced both in the deflection wedge 606 and/or on the surface 609 of the inner chamber 604. In FIG. 8, the flow $u_1$ of the delivered external air, the flow of the fed-in auxiliary gas oxygen $u_2$ and the flow of the respiratory gas $u_3$ are each illustrated in the drawing by differently formed arrows. In the labyrinth 605, the flow $u_1$ of the delivered external air has one deflection r, the flow $u_2$ of the fed-in auxiliary gas oxygen has two deflections r, and the flow $u_3$ of the respiratory gas has three deflections. The deflections ensure that the sound waves are reflected back and cannot propagate unimpeded. The flow $u_2$ of the fed-in auxiliary gas oxygen is deflected at least twice, preferably three times; it is deflected at least once by more than 45°, preferably more than 70° and for example 90° and is deflected at least one more time by more than 45°, preferably more than 70°, for example 90° and, finally, is deflected by more than 45°, preferably more than 70°, for example 100°.

The flow $u_1$ of the delivered external air is deflected at least once by more than about 45°, preferably more than about 70°, for example about 90°.

The flow $u_3$ of the respiratory gas (O2/air mixture) is deflected at least twice, preferably three times; it is deflected at least once by more than about 45°, preferably more than about 70°, for example about 90° and is deflected at least one more time by more than about 45°, preferably more than about 70°, for example about 90° and, finally, is deflected by more than about 45°, preferably more than about 70°, for example about 90° or about 180°.

Here, the flow $u_2$ of the fed-in auxiliary gas oxygen is likewise routed around the wedge tip 607, as a result of which good mixing is particularly advantageously achieved at the same time. By deflections r, a reflection of sound waves during operation of the electric fan 2 is effected, which particularly advantageously permits acoustic damping of the operated respirator 1.

The partition wall 617 is arranged adjacent to the wedge tip 607. For example, a constriction forms here in the flow cross section. The partition wall 617 separates the valve off from the stream of oxygen $u_2$.

When the stream of oxygen is very great by comparison with that of the ambient air $u_1$, the partition wall is intended to prevent a negative influence on the sealing function of the valve. The partition wall 617 has a side 617a, which faces toward the oxygen stream $u_2$, and a side 617b, which is directed toward the stream of the ambient air $u_1$. With its tip 617c, the partition wall 617 points into the inner chamber 604, wherein the oxygen stream $u_2$ and the ambient air $u_1$ meet and mix at the tip 617c of the partition wall.

FIG. 9 shows a sectioned oblique view of the mixing chamber 6 of the third illustrative embodiment, in which the valve 3 is integrated, and illustrates changes of a respective cross section $Q_1$, $Q_2$, $Q_3$, $Q_4$ and $Q_5$ through which gas flows. In FIG. 9, the cross sections $Q_1$, $Q_2$, $Q_3$, $Q_4$ and $Q_5$ through which the delivered external air and the fed-in oxygen flow are shown as surfaces in order to illustrate their geometries, and they are depicted at the same relative scale in order to illustrate their size relationships to one another, wherein the positions of these individual cross sections $Q_1$, $Q_2$, $Q_3$, $Q_4$ and $Q_5$ in the mixing chamber 6 are depicted by target arrows in the drawing of the mixing chamber 6. In the labyrinth 605, the flow $u_1$ of the delivered external air, the flow $u_2$ of the fed-in auxiliary gas oxygen and the flow $u_3$ of the respiratory gas have at least once a change of the respective cross sections $Q_1$, $Q_2$, $Q_3$, $Q_4$ and $Q_5$ vertically with respect to the direction of flow d, as a result of which a further improvement of the acoustic damping is provided.

The cross sections $Q_1$, $Q_2$, $Q_3$, $Q_4$ and $Q_5$ correspond to cross sections of flow. The laminar stream through the mixing chamber 6 is also achieved particularly advantageously at the same time, by virtue of the fact that the cross section of flow both of the port for the gas-dosing unit 5 and of the port 603 for the supply line 7 correspond to the cross section of flow S of the inlet 302 and of the outlet 303 of the valve 3 in terms of surface area and geometry. Thus, the mixing chamber 6 of the third illustrative embodiment is optimized both in terms of a reduced overall size and also in terms of acoustic insulation, while the laminar stream is obtained at the same time.

The flow $u_1$ of the delivered external air enters the inlet 302 with a relatively large cross section of flow S, wherein the inlet has a round cross section, for example. The flow $u_1$ of the delivered external air passes the valve, wherein the flow cross section here decreases for example, but wherein preferably no constriction arises in the region of the valve 3.

The flow $u_1$ passes farther along the partition wall 617 and, at the tip 617c of the partition wall 617, meets the flow $u_2$ of the fed-in auxiliary gas. Downstream from the mixing site, the flow cross section decreases as far as the cross section $Q_4$. The flow $u_3$ of the mixed respiratory gas then deflects three times and leaves the mixing chamber through the port 603.

In a fourth illustrative embodiment, the valve 3 is configured as a proportional valve. This particularly advantageously permits precise setting and/or readjustment of fixed pressure and/or flow values of the anesthetic gas or of the respiratory gas by adjusting the distance a between the sealing plate 308 and the flange seal 313 through regulation of the current strength at the lifting electromagnet 304. The laminar stream is then obtained to a sufficient extent even when the mathematical product of the circumference of the sealing plate and the distance a between the sealing plate 308 and the edge 315 of the inlet deviates by not more than 20% from the cross section of flow S of the inlet 302.

FIG. 10 shows a side view of a structural part 601 produced by form-fit and force-fit engagement, for example a mixing chamber housing 601, composed of a construction piece 610 and a mating piece 611. The construction piece 610 has a connecting edge 612 and the mating piece 611 has a connecting edge 613, each of these edges having a form-fit match to each other. In this structural part 601 produced from the construction piece 610 and the mating piece 611, the design is additionally such that the openings for the ports 602 and the inlet 302 are divided by the connecting edges 612, 613. The construction piece 610 and the mating piece 611 are produced from ABS.

FIG. 11 shows a plan view of a connecting edge 612 of the construction piece 610 from FIG. 10, illustrating the connecting edge 612 with a groove 614, a transverse groove 615 and a flat seal 616. On the right, FIG. 11 shows a detail from the connecting edge 612 at the site of the port 603 for the supply line 7, while at the top left and bottom left it shows in each case an enlarged view of the groove 614 with the transverse groove 615 of the flat seal 616.

At the site of the construction piece 610 shown in FIG. 11, a groove 614 is let into a connecting edge 612 and runs parallel to the length of the connecting edge 612, and a transverse groove 615 is let in which opens vertically into the groove 614 and interrupts the associated connecting edge 612, wherein an elastic and compressible one-piece flat seal 616 is introduced extending both in the groove 614 and in the respective transverse groove 615. The flat seal 616 is produced from silicone. The flat seal 616 has a form-fit match both to the groove 614 and to each transverse groove 615. The flat seal 616 has a sealing height h greater than the depth $n_1$ of the groove 614 and the depth $n_2$ of the transverse groove 615. In this illustrative embodiment, the sealing height is 1.2 times the depth $n_1$ of the groove 614, wherein the depth $n_1$ of the groove 614 is equal to the depth $n_2$ of the transverse groove 615. The flat seal 616 is configured protruding above the transverse groove 615 through the connecting edge 612 by 1.2 times the depth $n_2$ of the transverse groove 615. By compression of the flat seal 616 in the transverse groove 615 through form-fit and force-fit connection to form the structural part 601, the seal is strengthened at the associated site of the connecting edge 612.

To sum up, the present invention provides the following items:

1. A respirator which comprises an electronic control device and a pneumatic main line in which the following are connected pneumatically: a respiratory gas source, at least one valve, a mixing chamber, a gas-dosing unit, and a supply line, and wherein the gas-dosing unit is configured to convey external air and/or oxygen and/or anesthetic gas into the mixing chamber, the respiratory gas source is configured to deliver respiratory gas to the supply line, the mixing chamber is configured to make available respiratory gas, the supply line is configured to supply the patient with respiratory gas, and the at least valve is configured to at least temporarily reduce a stream of respiratory gas to a patient, the respiratory gas comprising external air and/or oxygen and/or anesthetic gas.

2. The respirator of item 1, wherein the mixing chamber is configured to make available respiratory gas by mixing external air and/or oxygen and/or anesthetic gas.

3. The respirator of item 1 or item 2, wherein the respiratory gas source is positioned in the pneumatic main line and configured as an electric fan, a fan output is connected pneumatically to the at least one valve, which valve is connected pneumatically to the mixing chamber which in turn is connected pneumatically both to the gas-dosing unit and to the supply line, the input of the electric fan is configured to make available external air, the gas-dosing unit is configured for adjustable pneumatic feeding of an oxygen-containing auxiliary gas in addition to or instead of delivered external air into the mixing chamber, the supply line is configured to supply the patient with a respiratory gas consisting of the delivered external air or a gas mixture of the external air and the auxiliary gas or the auxiliary gas alone, and the at least one valve is configured to at least temporarily reduce or interrupt a stream of external air into the mixing chamber.

4. The respirator of any one of the preceding items, wherein the respiratory gas source is configured as an electric fan and wherein the at least one valve is configured as part of the mixing chamber or is arranged in a common housing of the mixing chamber, the valve in the pneumatic main line is arranged downstream from a fan output in a direction of flow (d) and upstream from the gas-dosing unit in a direction of flow (d), and the gas-dosing unit is arranged upstream from the supply line in a direction of flow (d).

5. The respirator of any one of the preceding items, wherein the respiratory gas source is configured as an electric fan and wherein, in a direction of flow (d) in the pneumatic main line, a fan output is connected pneumatically to the at least one valve, which valve is connected pneumatically to the mixing chamber, which in turn is connected pneumatically both to the gas-dosing unit and to the supply line, a suction input is configured to deliver external air, the gas-dosing unit is configured for adjustable pneumatic feeding of an oxygen-containing auxiliary gas in addition to or instead of delivered external air into the mixing chamber, the supply line is configured to supply the patient with a respiratory gas consisting of the delivered external air or a gas mixture of the external air and the auxiliary gas or the auxiliary gas alone, the control device can be used to adjust the auxiliary gas fraction, the respiration pressure and a respiration flow of the respiratory gas, and is additionally configured to shut off the at least one valve with simultaneous opening of the gas-dosing unit, which gas-dosing unit itself is configured to make available respiratory gas in the event of a failure of the electric fan and/or of the power supply and/or in the event of a failure of a processor and/or in the event of a software crashing.

6. The respirator of any one of the preceding items, wherein the mixing chamber comprises a port for the gas-dosing unit, a port for the supply line, and a port for the respiratory gas source.

7. The respirator of any one of the preceding items, wherein, the mixing chamber comprises at least one port for connection to a component, which port comprises a releasable closure for rapid mounting of the component.

8. The respirator of any one of the preceding items, wherein the respiratory gas source is configured as an electric fan and the at least one valve, comprising an inlet and an outlet in a valve housing, is connected pneumatically via the outlet to a suction input or via the inlet to a fan output, the electric fan and the at least one valve are electronically regulated with the control device in at least one common control circuit, the control device itself can be electronically regulated and/or automatically regulated at least partially with a processor via an algorithm in the form of software, and functional assemblies and optionally measuring and/or regulating instruments are connected pneumatically in or on the pneumatic main line and/or in further pneumatic branch lines and/or secondary lines and/or return lines, the functional assemblies being electronically regulated by the control device, and the measuring and/or regulating instruments being likewise optional assemblies of the control device.

9. The respirator of any one of the preceding items, wherein the valve is configured as a nonreturn valve and/or as a solenoid valve and/or as a proportional valve.

10. The respirator of any one of the preceding items, wherein the respiratory gas source is configured as an electric fan and the at least one valve is configured as a solenoid valve with an electromagnet fixed in a valve housing and with a magnetically movable valve piston, the valve piston comprising a sealing plate with a seal, which sealing plate acts on an inlet, and wherein the valve piston is pressed with the sealing plate against the inlet by a spring, such that a gas flow from or to the electric fan is suppressed.

11. The respirator of any one of the preceding items, wherein the electromagnet, in the a state of the solenoid valve, is currentless.

12. The respirator of any one of the preceding items, wherein, when current flows through the electromagnet, an adjustable or predetermined magnetic force acts on the magnetically movable valve piston, which magnetically movable valve piston compresses the spring to a predefinable extent, and wherein, in an opened state, a magnetic force acting on the magnetically movable valve piston is greater than a force of the spring.

13. The respirator of any one of the preceding items, wherein the respiratory gas source is configured as an electric fan and the control device comprises at least one processor (or computer) or comprises several processors, in order to control at least the electric fan, the at least one valve and measuring and/or regulating instruments and/or wherein the control device is configured to automatically shut off the at least one valve in the event of a failure of the electric fan and/or in the event of a failure of the control device.

14. The respirator of any one of the preceding items, wherein the respiratory gas source is configured as an electric fan and wherein, in a direction of flow (d), the gas-dosing unit is connected pneumatically to the mixing chamber which in turn is connected pneumatically to a suction input of the electric fan, which fan output is connected pneumatically to the supply line and they thus form the pneumatic main line, wherein the at least one valve is connected pneumatically upstream from the suction input or downstream from the fan output, or two valves are each connected pneumatically upstream from the suction input and downstream from the fan output in the pneumatic main line, wherein the gas-dosing unit is configured to pneumatically feed gases into the mixing chamber, which mixing chamber is configured to mix an anesthetic gas from fed-in gases, and the suction input is configured to deliver anesthetic gas, wherein the supply line is configured to supply the patient with anesthetic gas, the anesthetic gas containing oxygen and at least one anesthetic agent, wherein the control device can be used to adjust a pneumatic feed of gases independently of each other and to adjust a respiration pressure and a respiration flow of the anesthetic gas, and wherein the control device (8) is additionally configured to automatically shut off the gas-dosing unit in the event of a failure of the electric fan and/or of the power supply and/or in the event of a failure of a processor and/or in the event of a software crashing.

15. The respirator of any one of the preceding items, wherein the respiratory gas source is configured as an electric fan and wherein, in a direction of flow (d) in the pneumatic main line, a fan output is connected pneumatically to the at least one valve, which valve is connected pneumatically to a mixing chamber, which in turn is connected pneumatically both to the gas-dosing unit and to the supply line, wherein a suction input is configured to deliver external air, wherein the gas-dosing unit is configured for adjustable pneumatic feeding of an oxygen-containing auxiliary gas in addition to or instead of delivered external air into the mixing chamber, wherein the supply line is configured to supply the patient with a respiratory gas consisting of the delivered external air or a gas mixture of the external air and the auxiliary gas or the auxiliary gas alone, wherein the control device can be used to adjust an auxiliary gas fraction, a respiration pressure and a respiration flow of the respiratory gas, and wherein the control device is additionally configured to automatically shut off the at least one valve with simultaneous opening of the gas-dosing unit, and the gas-dosing unit itself is configured for a fully automatic and/or partially assisted ventilation of a patient in the event of a failure of the electric fan and/or of the power supply and/or in the event of a failure of a processor and/or in the event of a software crashing.

16. The respirator of any one of the preceding items, wherein the at least one valve is directly controlled, for which purpose it comprises a lifting electromagnet with a valve piston and can be operated by current regulation at the lifting magnet, wherein a sealing plate is mounted vertically on a front of the valve piston, wherein an inlet is configured as a valve seat, wherein the sealing plate is given mechanical play with three degrees of freedom, wherein the inlet and also an outlet each have an identical cross section of flow (S) with respect to surface area, wherein, in an opened state of the at least one valve, a gas flow is permitted both on a side of the sealing plate facing toward the inlet and also to a rear thereof, and a mathematical product of a circumference of the sealing plate and a distance (a) between the sealing plate and an edge of the inlet corresponds to the cross section of flow (S) with a deviation of not more than 20%.

17. The respirator of any one of the preceding items, wherein the at least one valve is configured as a nonreturn valve for shutting off the respiratory gas source configured as an electric fan in the event of a failure of the power supply and/or in the event of the outlet having an overpressure relative to the inlet.

18. The respirator of any one of the preceding items, wherein the mixing chamber is configured as a valve housing, wherein an inlet of the at least one valve is configured as an inlet to the mixing chamber, and an outlet of the at least one valve is guided pneumatically into an inner chamber of the mixing chamber, the inner chamber being connected pneumatically both to the gas-dosing unit and to the supply line, and optionally comprising a labyrinth.

19. The respirator of any one of the preceding items, wherein, in the labyrinth, a flow ($u_1$) of delivered external air and/or a flow of fed-in auxiliary gas ($u_2$) and/or a flow of the respiratory gas ($u_3$) in each case has at least once a deflection (r), and/or the flow ($u_1$) and/or the flow ($u_2$) and/or the flow ($u_3$) has at least once a change of the flow cross section ($Q_1$, $Q_2$, $Q_3$, $Q_4$, $Q_5$) vertically with respect to a direction of flow (d).

20. The respirator of any one of the preceding items, wherein the mixing chamber upstream from the gas-dosing unit has a deflection wedge with a wedge tip, a flow ($u_2$) of fed-in auxiliary gas being routed around the wedge tip and the deflection wedge being configured with a hollow shape and/or comprising a filler composed of insulating material.

21. The respirator of any one of the preceding items, wherein, in the labyrinth, a surface is provided which is at least partially lined with insulating material and/or which optionally has antimicrobial properties at least in subregions, and/or wherein the insulating material optionally has antimicrobial properties.

22. A respirator which comprises a pneumatic main line in which the following are connected pneumatically: a respiratory gas source, at least one valve, a mixing chamber, a gas-dosing unit and a supply line, the mixing chamber being configured as a valve housing, an inlet of the at least one valve (3) being configured as an inlet to the mixing chamber, and an outlet of the at least one valve being guided pneumatically into an inner chamber of the mixing chamber, which inner chamber is connected pneumatically both to the gas-dosing unit and to the supply line, and optionally comprises a labyrinth.

23. A mixing chamber for the respirator of any one of items 1 to 22, wherein the mixing chamber comprises a mixing chamber housing which has a port for the gas-dosing unit, a port for the supply line, and a port for the respiratory gas source.

24. A mixing chamber for a respirator, which mixing chamber comprises a structural part, for example a mixing chamber housing, which is produced from a construction piece and a mating piece by form-fit and force-fit engagement, wherein the construction piece and the mating piece each have connecting edges that engage each other with a form fit, wherein, in the construction piece, a groove is let at least into a connecting edge and runs parallel to a length of the connecting edge, and a transverse groove is let in which opens vertically into the groove and interrupts an associated connecting edge, wherein an elastic and compressible one-piece flat seal is introduced extending both in the groove and in a transverse groove, wherein the flat seal has a form-fit match both to the groove and to the transverse groove, wherein the flat seal has a sealing height (h) greater than a depth ($n_1$) of the groove and a depth ($n_2$) of the transverse groove and at most corresponding both to twice the depth ($n_1$) of the groove and twice the depth ($n_2$) of the transverse groove, and wherein the flat seal is accordingly configured protruding above the transverse groove through the connecting edge by not more than twice the depth of the transverse groove.

LIST OF REFERENCE SIGNS 1 respirator
2 electric fan
21 suction input
22 fan output
3 (solenoid) valve
301 valve housing
302 inlet
303 outlet
304 lifting electromagnet
305 valve piston
306 restoring spring
307 ball
308 sealing plate
309 ball socket
310 sealing edge
311 ball joint
312 valve seat
313 flange seal
314 free spaces
315 edge
4 pneumatic main line
5 gas-dosing unit
51 feed input for external air
52 feed input for oxygen
53 feed input for anesthetic gas (nitrous oxide)
6 mixing chamber
601 mixing chamber housing
620 port for respiratory gas source 2
602 port for gas-dosing unit 5
603 port for supply line 7
604 inner chamber 605 labyrinth
606 deflection wedge
607 wedge tip
608 insulating material (macroporous foam)
609 surface
610 construction piece
611 mating piece
612 connecting edge of the construction piece 610
613 connecting edge of the mating piece 611
614 groove
615 transverse groove
616 flat seal
617 partition wall
618 cul-de-sac
7 supply line
8 control
a distance
d direction of flow
h sealing height
l longitudinal axis
$n_1$ depth of the groove 614
$n_2$ depth of the transverse groove 615
$Q_1$ cross section
$Q_2$ cross section
$Q_3$ cross section
$Q_4$ cross section
$Q_5$ cross section
r deflection
S cross section of flow
$u_1$ flow of the delivered external air
$u_2$ flow of the fed-in auxiliary gas
$u_3$ flow of the respiratory gas

What is claimed is:

1. A respirator, wherein the respirator comprises an electronic control device and a pneumatic main line in which the following are connected pneumatically: a respiratory gas source, at least one valve, a mixing chamber, a gas-dosing unit, and a supply line, and wherein the gas-dosing unit is configured to convey external air and/or oxygen and/or anesthetic gas into the mixing chamber, the respiratory gas source is configured to deliver respiratory gas to the supply line, the mixing chamber is configured to make available the respiratory gas, the supply line is configured to supply a patient with the respiratory gas, and the at least valve is configured to at least temporarily reduce a stream of the respiratory gas to the patient, the respiratory gas comprising external air and/or oxygen and/or anesthetic gas, and wherein the respiratory gas source is configured as an electric fan and wherein the at least one valve is configured as part of the mixing chamber or is arranged in a common housing of the mixing chamber, the at least one valve in the pneumatic main line is arranged downstream from a fan output in a direction of flow (d) and upstream from the gas-dosing unit in the direction of flow (d), and the gas-dosing unit is arranged upstream from the supply line in the direction of flow (d).

2. The respirator of claim 1, wherein the mixing chamber comprises at least one port for connection to a component, which port comprises a releasable closure for rapid mounting of the component.

3. The respirator of claim 1, wherein the at least one valve is configured as a solenoid valve with an electromagnet fixed in a valve housing and with a magnetically movable valve piston, the valve piston comprising a sealing plate with a seal, which sealing plate acts on an inlet, and wherein the valve piston is pressed with the sealing plate against the inlet by a spring, such that a gas flow from or to the electric fan is suppressed.

4. The respirator of claim 3, wherein the electromagnet, in a closed state of the solenoid valve, is currentless.

5. The respirator of claim 3, wherein, when current flows through the electromagnet, an adjustable or predetermined magnetic force acts on the magnetically movable valve piston, which magnetically movable valve piston compresses the spring to a predefined extent, and wherein, in an opened state, a magnetic force acting on the magnetically movable valve piston is greater than a force of the spring.

6. The respirator of claim 1, wherein the mixing chamber is configured as a valve housing, wherein an inlet of the at least one valve is configured as an inlet to the mixing chamber, and an outlet of the at least one valve is guided pneumatically into an inner chamber of the mixing chamber, the inner chamber being connected pneumatically both to the gas-dosing unit and to the supply line, and optionally comprising a labyrinth.

7. The respirator of claim 6, wherein, in the labyrinth, a flow ($u_1$) of delivered external air and/or a flow of fed-in auxiliary gas ($u_2$) and/or a flow of the respiratory gas ($u_3$) in each case has at least once a deflection (r), and/or the flow ($u_1$) and/or the flow ($u_2$) and/or the flow ($u_3$) has at least once a change of the flow cross section ($Q_1$, $Q_2$, $Q_3$, $Q_4$, $Q_5$) vertically with respect to a direction of flow (d).

8. The respirator of claim 1, wherein the mixing chamber comprises a mixing chamber housing which has a port for the gas-dosing unit, a port for the supply line, and a port for the respiratory gas source.

9. A respirator, wherein the respirator comprises an electronic control device and a pneumatic main line in which the following are connected pneumatically: a respiratory gas source, at least one valve, a mixing chamber, a gas-dosing unit, and a supply line, and wherein the gas-dosing unit is configured to convey external air and/or oxygen and/or anesthetic gas into the mixing chamber, the respiratory gas source is configured to deliver respiratory gas to the supply line, the mixing chamber is configured to make available the respiratory gas, the supply line is configured to supply a patient with the respiratory gas, and the at least valve is configured to at least temporarily reduce a stream of the respiratory gas to the patient, the respiratory gas comprising external air and/or oxygen and/or anesthetic gas, and wherein the respiratory gas source is configured as an electric fan and wherein, in a direction of flow (d) in the pneumatic main line, a fan output is connected pneumatically to the at least one valve, which valve is connected pneumatically to the mixing chamber, which in turn is connected pneumatically both to the gas-dosing unit and to the supply line, a suction input is configured to deliver external air, the gas-dosing unit is configured for adjustable pneumatic feeding of an oxygen-containing auxiliary gas in addition to or instead of delivered external air into the mixing chamber, the supply line is configured to supply the patient with a respiratory gas consisting of the delivered external air or a gas mixture of the external air and the auxiliary gas or the auxiliary gas alone, the electronic control device is configured to be used to adjust an auxiliary gas fraction, a respiration pressure and a respiration flow of the respiratory gas, and is additionally configured to shut off the at least one valve with simultaneous opening of the gas-dosing unit, which gas-dosing unit itself is configured to make available the respiratory gas in the event of a failure of the electric fan and/or of a power supply and/or in the event of a failure of a processor and/or in the event of a software crashing.

10. The respirator of claim 9, wherein the mixing chamber comprises a mixing chamber housing which has a port for the gas-dosing unit, a port for the supply line, and a port for the respiratory gas source.

11. The respirator of claim 9, wherein the at least one valve is configured as a solenoid valve with an electromagnet fixed in a valve housing and with a magnetically movable valve piston, the valve piston comprising a sealing plate with a seal, which sealing plate acts on an inlet, and wherein the valve piston is pressed with the sealing plate against the inlet by a spring, such that a gas flow from or to the electric fan is suppressed.

12. A respirator, wherein the respirator comprises an electronic control device and a pneumatic main line in which the following are connected pneumatically: a respiratory gas source, at least one valve, a mixing chamber, a gas-dosing unit, and a supply line, and wherein the gas-dosing unit is configured to convey external air and/or oxygen and/or anesthetic gas into the mixing chamber, the respiratory gas source is configured to deliver respiratory gas to the supply line, the mixing chamber is configured to make available the respiratory gas, the supply line is configured to supply a patient with the respiratory gas, and the at least valve is configured to at least temporarily reduce a stream of the respiratory gas to the patient, the respiratory gas comprising external air and/or oxygen and/or anesthetic gas, and wherein the respiratory gas source is configured as an electric fan and the control device comprises at least one processor or computer or comprises several processors, in order to control at least the electric fan, the at least one valve and measuring and/or regulating instruments and/or wherein the electronic control device is configured to automatically shut off the at least one valve in the event of a failure of the electric fan and/or in the event of a failure of the electronic control device.

13. The respirator of claim 12, wherein the mixing chamber comprises a mixing chamber housing which has a port for the gas-dosing unit, a port for the supply line, and a port for the respiratory gas source.

14. The respirator of claim 12, wherein the at least one valve is configured as a solenoid valve with an electromagnet fixed in a valve housing and with a magnetically movable valve piston, the valve piston comprising a sealing plate with a seal, which sealing plate acts on an inlet, and wherein the valve piston is pressed with the sealing plate against the inlet by a spring, such that a gas flow from or to the electric fan is suppressed.

15. A respirator, wherein the respirator comprises an electronic control device and a pneumatic main line in which the following are connected pneumatically: a respiratory gas source, at least one valve, a mixing chamber, a gas-dosing unit, and a supply line, and wherein the gas-dosing unit is configured to convey external air and/or oxygen and/or anesthetic gas into the mixing chamber, the respiratory gas source is configured to deliver respiratory gas to the supply line, the mixing chamber is configured to make available the respiratory gas, the supply line is configured to supply a patient with the respiratory gas, and the at least valve is configured to at least temporarily reduce a stream of the respiratory gas to the patient, the respiratory gas comprising external air and/or oxygen and/or anesthetic gas, and wherein the respiratory gas source is configured as an electric fan and wherein, in a direction of flow (d) in the pneumatic main line, a fan output is connected pneumatically to the at least one valve, which valve is connected pneumatically to the mixing chamber, which in turn is connected pneumatically both to the gas-dosing unit and to the supply line, wherein a suction input is configured to deliver external air, wherein the gas-dosing unit is configured for adjustable pneumatic feeding of an oxygen-containing auxiliary gas in addition to or instead of delivered external air into the mixing chamber, wherein the supply line is configured to supply the patient with the respiratory gas consisting of the delivered external air or a gas mixture of the external air and the auxiliary gas or the auxiliary gas alone, wherein the electronic control device is configured to be used to adjust an auxiliary gas fraction, a respiration pressure and a respiration flow of the respiratory gas, and wherein the electronic control device is additionally configured to automatically shut off the at least one valve with simultaneous opening of the gas-dosing unit, and the gas-dosing unit itself is configured for a fully automatic and/or partially assisted ventilation of the patient in the event of a failure of the electric fan and/or of a power supply and/or in the event of a failure of a processor and/or in the event of a software crashing.

16. The respirator of claim 15, wherein the mixing chamber comprises a mixing chamber housing which has a port for the gas-dosing unit, a port for the supply line, and a port for the respiratory gas source.

17. The respirator of claim 15, wherein the at least one valve is configured as a solenoid valve with an electromagnet fixed in a valve housing and with a magnetically movable valve piston, the valve piston comprising a sealing plate with a seal, which sealing plate acts on an inlet, and wherein the valve piston is pressed with the sealing plate against the inlet by a spring, such that a gas flow from or to the electric fan is suppressed.

18. A respirator, wherein the respirator comprises an electronic control device and a pneumatic main line in which the following are connected pneumatically: a respiratory gas source, at least one valve, a mixing chamber, a gas-dosing unit, and a supply line, and wherein the gas-dosing unit is configured to convey external air and/or oxygen and/or anesthetic gas into the mixing chamber, the respiratory gas source is configured to deliver respiratory gas to the supply line, the mixing chamber is configured to make available the respiratory gas, the supply line is configured to supply a patient with the respiratory gas, and the at least valve is configured to at least temporarily reduce a stream of the respiratory gas to the patient, the respiratory gas comprising external air and/or oxygen and/or anesthetic gas, and wherein the at least one valve is directly controlled, for which purpose it comprises a lifting electromagnet with a valve piston and is configured to be operated by current regulation at the lifting electromagnet, wherein a sealing plate is mounted vertically on a front of the valve piston, wherein an inlet is configured as a valve seat, wherein the sealing plate is given mechanical play with three degrees of freedom, wherein the inlet and also an outlet each have an identical cross section of flow(S) with respect to surface area, wherein, in an opened state of the at least one valve, a gas flow is permitted both on a side of the sealing plate facing toward the inlet and also to a rear thereof, and a mathematical product of a circumference of the sealing plate and a distance (a) between the sealing plate and an edge of the inlet corresponds to the cross section of flow(S) with a deviation of not more than 20%.

19. The respirator of claim 18, wherein the mixing chamber comprises a mixing chamber housing which has a port for the gas-dosing unit, a port for the supply line, and a port for the respiratory gas source.

20. The respirator of claim 18, wherein the at least one valve is configured as a solenoid valve with an electromagnet fixed in a valve housing and with a magnetically movable valve piston, the valve piston comprising a sealing plate with a seal, which sealing plate acts on an inlet, and wherein the valve piston is pressed with the sealing plate against the inlet by a spring, such that a gas flow from or to the electric fan is suppressed.

* * * * *